United States Patent
Eberwine et al.

(10) Patent No.: US 9,540,680 B2
(45) Date of Patent: *Jan. 10, 2017

(54) TRANSCRIPTOME IN VIVO ANALYSIS

(71) Applicant: THE TRUSTEES OF THE UNIVERSITY OF PENNSYLVANIA, Philadelphia, PA (US)

(72) Inventors: James Eberwine, Philadelphia, PA (US); Ditte Lovatt, Swarthmore, PA (US); Julia Richards, Philadelphia, PA (US); Ivan Dmochowski, Philadelphia, PA (US); Brittani Ruble, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/838,504

(22) Filed: Mar. 15, 2013

(65) Prior Publication Data
US 2013/0273537 A1 Oct. 17, 2013

Related U.S. Application Data

(63) Continuation-in-part of application No. 13/702,415, filed as application No. PCT/US2011/039447 on Jun. 7, 2011.

(60) Provisional application No. 61/352,199, filed on Jun. 7, 2010, provisional application No. 61/614,940, filed on Mar. 23, 2012.

(51) Int. Cl.
C12N 15/10 (2006.01)
C12Q 1/68 (2006.01)

(52) U.S. Cl.
CPC ........... C12Q 1/6806 (2013.01); C12Q 1/6876 (2013.01); *C12Q 2600/124* (2013.01)

(58) Field of Classification Search
CPC ..... C12Q 1/6806; C12Q 1/6876; A61K 38/00; A61K 51/088; C12N 15/10; C12N 15/1003; C12N 15/11; C12N 2310/3513; C12N 2310/3517
See application file for complete search history.

(56) References Cited

U.S. PATENT DOCUMENTS

| 2008/0227742 | A1 | 9/2008 | Dmochowski et al. |
| 2008/0234183 | A1* | 9/2008 | Hallbrink ........... A61K 51/0448 514/1.1 |
| 2009/0087899 | A1 | 4/2009 | McKnight et al. |
| 2009/0092660 | A1* | 4/2009 | Mrsny ................. A61K 9/0053 424/450 |

(Continued)

FOREIGN PATENT DOCUMENTS

WO WO2011/156376 12/2011

OTHER PUBLICATIONS

Richards et al., Turning the 10-23 DNAzyme On and Off with Light, Chembiochem, 11(3):320-324 (Feb. 15, 2010).*

(Continued)

*Primary Examiner* — James H Alstrum Acevedo
*Assistant Examiner* — Randall L Beane
(74) *Attorney, Agent, or Firm* — Riverside Law LLP

(57) ABSTRACT

The invention provides compositions and methods that permit a hybrid nucleic acid molecule to enter a cell and when specifically activated within the cell, the molecule anneals to endogenous cellular RNA and permits the isolation of the RNA.

26 Claims, 27 Drawing Sheets

(56) References Cited

U.S. PATENT DOCUMENTS

2009/0317906 A1    12/2009  Weber et al.
2010/0190691 A1*    7/2010  Epenetos ......... A61K 47/48246
                                                          514/1.1

OTHER PUBLICATIONS

Kubo et al., Efficient Cleavage of RNA, enhanced cellular uptake, and controlled intracellular localization of conjugate DNAzymes, Bioorganic & Medicinal Chemistry Letters, 15:167-170 (2005).*
Dalavoy et al., Immobilization of DNAzyme catalytic beacons on PMMA for PB2+ detection, Lab Chip, 8:786-793 (2008).*
Allinquant et al, Downregulation of Amyloid Precursor Protein Inhibits Neurite Outgrowth In Vitro, The Journal of Cell Biology, vol. 128:919-927 (Mar. 1, 1995).*
Grokhovsky et al, Sequence-specific cleavage of double-stranded DNA caused by X-ray ionization of the platinum atom in the Pt-Bis-netropsin-DNA complex, Nucleic Acids Research, vol. 19(2):257-264 (1991).*
Stewart et al., Cell-penetrating peptides as delivery vehicles for biology and medicine, Org. Biomol. Chem., (Apr. 2008) vol. 6:2242-2255.*
Bao et al., Fluorescent Probes for Live-Cell RNA Detection, Annu. Rev. Biomed. Eng., (Mar. 31, 2009) vol. 11:25-47.*
Li et al, Folate-Mediated Targeting of Antisense Oligodeoxynucleotides to Ovarian Cancer cells, Pharmaceutical Research, vol. 15(10):1540-1545 (1998).*
Dictionary.com, "Substantial", dictionary.reference.com, attached as pdf, also available at http://dictionary.reference.com/browse/substantially, last visited Nov. 5, 2014.*
Zuker, Mfold web server for nucleic acid folding and hybridization prediction, Nucleic Acids Res. 31 (13), 3406-15, (2003); web server available at http://unafold.rna.albany.edu/?q=mfold/DNA-Folding-Form (last visited Jan. 14, 2016).*
Bach, et al., "Magnetic capture-hybridization method for purification and probing of mRNA for neutral protease of Bacillus cereus," J. Microbiol Methods, 1999, 37:187-192.
Kaern et al., "Stochasticity in gene expression: from theories to phenotypes," Nat. Rev. Genet., 6:451-464 (2005).
Raj et al., "Nature, nurture, or chance: stochastic gene expression and its consequences," Cell, 135:216-226 (2008).
Elowitz et al., "Stochastic gene expression in a single cell," Science, 297:1183-1186 (2002).
Pedraza et al., "Noise propagation in gene networks," Science, 307:1965-1969 (2005).
Cahoy et al., "A transcriptome database for astrocytes, neurons, and oligodendrocytes: a new resource for understanding brain development and function," J. Neurosci., 28:264-278 (2008).
Lovatt et al., "The transcriptome and metabolic gene signature of protoplasmic astrocytes in the adult murine cortex," J. Neurosci., 27:12255-12266 (2007).
Sugino et al., "Molecular taxonomy of major neuronal classes in the adult mouse forebrain," Nat. Neurosci., 9:99-107 (2006).
Espina et al., "Laser-capture microdissection," Nat. Protoc., 1:586-603 (2006).
Joliot et al., "Transduction peptides: from technology to physiology," Nat. Cell Biol., 6:189-196 (2004).
Kumar et al., "Transvascular delivery of small interfering RNA to the central nervous system," Nature, 448:39-43 (2007).
Zeng et al., "A protocol for PAIR: PNA-assisted identification of RNA binding proteins in living cells," Nat. Protoc., 1:920-927 (2006).
Zielinski et al., "In vivo identification of ribonucleoprotein-RNA interactions," Proc. Natl. Acad. Sci. USA, 103:1557-1562 (2006).
Adams et al., "Controlling cell chemistry with caged compounds," Annu. Rev. Physiol., 55:755-784 (1993).
Tang et al., "Synthesis of light-activated antisense oligodeoxynucleotide," Nat. Protoc., 1:3041-3048 (2006).

Dmochowski, et al., "Taking control of gene expression with light-activated oligonucleotides," Biotechniques, 43:161-165 (2007).
Roy et al., "A practical guide to single-molecule FRET," Nat. Methods, 5: 507-516 (2008).
Eberwine et al., "Analysis of gene expression in single live neurons," Proc. Natl. Acad. Sci. USA, 89:3010-3014(1992).
Ellis-Davies et al., "Caged compounds: photorelease technology for control of cellular chemistry and physiology," Nat. Methods, 4:619-628 (2007).
Zhang et al., "Defining glial cells during CNS development," Nat. Rev. Neurosci., 2:840-843 (2001).
Pribyl, et al., "Expression of the myelin basic protein gene locus in neurons and oligodendrocytes in the human fetal central nervous system," J. Comp. Neurol., 374:342-353 (1996).
Landry et al., "Myelin basic protein gene expression in neurons: developmental and regional changes in protein targeting within neuronal nuclei, cell bodies, and processes," The J. Neurosci., 16:2452-2462 (1996).
Vives et al., "Visualization of S100B-positive neurons and glia in the central nervous system of EGFP transgenic mice," J. Comp. Neurol., 457:404-419 (2003).
West et al., "Regulation of transcription factors by neuronal activity," Nat. Rev. Neurosci., 3:921-931 (2002).
Turner et al., "Cell-penetrating peptide conjugates of peptide nucleic acids (PNA) as inhibitors of HIV-1 Tat-dependent transactivation in cells," Nucleic Acids Res., 33:6837-6849 (2005).
Richards et al., "RNA bandages for photoregulating in vitro protein synthesis," Bioorg. Med. Chem. Lett., 18:6255-6258(2008).
Cummings et al., "Calcium-dependent paired-pulse facilitation of miniature EPSC frequency accompanies depression of EPSCs at hippocampal synapses in culture," J. Neurosci., 16:5312-5323 (1996).
Katayama et al., "A bromocoumarin-based linker for synthesis of photocleavable peptidoconjugates with high photosensitivity," Chemical Communications, 42:5399-401 (2008).
Eldar et al., "Functional roles for noise in genetic circuits," Nature, 467:167-173, Sep. 9, 2010.
Flatz. et al., "Single-cell gene-expression profiling reveals qualitatively distinct CD8 T cells elicited by different gene-based vaccines," Proc. Natl. Acad. Sci. USA, 108:5724-5729, Apr. 5, 2011; published online Mar. 21, 2011.
Taniguchi et al., "Quantifying E. coli proteome and transcriptome with single-molecule sensitivity in single cells," Science, 329:533-538, Jul. 30, 2010.
Eberwine et al., "Quantitative biology of single neurons," J. R. Soc. Interface, 9:3165-3183, Dec. 7, 2012; published online Aug. 22, 2012.
Tang, et al., "mRNA-seq whole-transcriptome analysis of a single cell," Nat. Methods, 6:377-382, May 2009; published online Apr. 6, 2009.
Okaty et al., "A quantitative comparison of cell-type-specific microarray gene expression profiling methods in the mouse brain," PLoS ONE, 6:e16493, Jan. 27, 2011.
Madani et al., "Mechanisms of cellular uptake of cell-penetrating peptides," J. Biophys., 2011:414729, 2011, published online Apr. 7, 2011.
Svensen et al., "Peptides for cell-selective drug delivery," Trends Pharmacol. Sci., 33:186-192, Apr. 2012, published online Mar. 15, 2012.
Morris et al., "Transcriptome analysis of single cells," J. Vis. Exp., 2011:2634, Apr. 25, 2011.
Ramskold et al., "Full-length mRNA-Seq from single-cell levels of RNA and individual circulating tumor cells," Nat. Biotechnol., 30:777-782, Aug. 2012; published online Jul. 22, 2012.
Griffith et al., "Alternative expression analysis by RNA sequencing," Nat. Methods, 7:843-847, Oct. 2010; published online Sep. 12, 2010.
Zheng et al., "Bias detection and correction in RNA-Sequencing data," BMC Bioinformatics, 12:290, Jul. 19, 2011.
Adiconis et al., "Comparative analysis of RNA sequencing methods for degraded or low-input samples," Nat. Methods, 10:623-629, Jul. 2013; published online May 19, 2013.

(56) References Cited

OTHER PUBLICATIONS

Gertz et al., "Transposase mediated construction of RNA-seq libraries," *Genome Res.*, 22:134-141, (2012), published online Nov. 29, 2011.
Grant et al., "Comparative analysis of RNA-Seq alignment algorithms and the RNA-Seq unified mapper (RUM)," *Bioinformatics*, 27:2518-2528, Sep. 15, 2011; published online Jul. 19, 2011.
Anders et al., "Differential expression analysis for sequence count data," *Genome Biol.*, 11:R106, (2010); published online Oct. 27, 2010.

\* cited by examiner

A

| B | Dye | Wavelength | Intensity | $I_a/(I_a+I_d)$ |
|---|---|---|---|---|
| Photolyzed | Cy3 | 565 | 33.20768 | $(I_d)$ |
| | Cy5 | 667 | 3.672207 | $(I_a)$ |
| | | | | 0.099572 |
| Un-photolyzed | Cy3 | 566 | 0.774745 | $(I_d)$ |
| | Cy5 | 668 | 1.168563 | $(I_a)$ |
| | | | | 0.601327 |

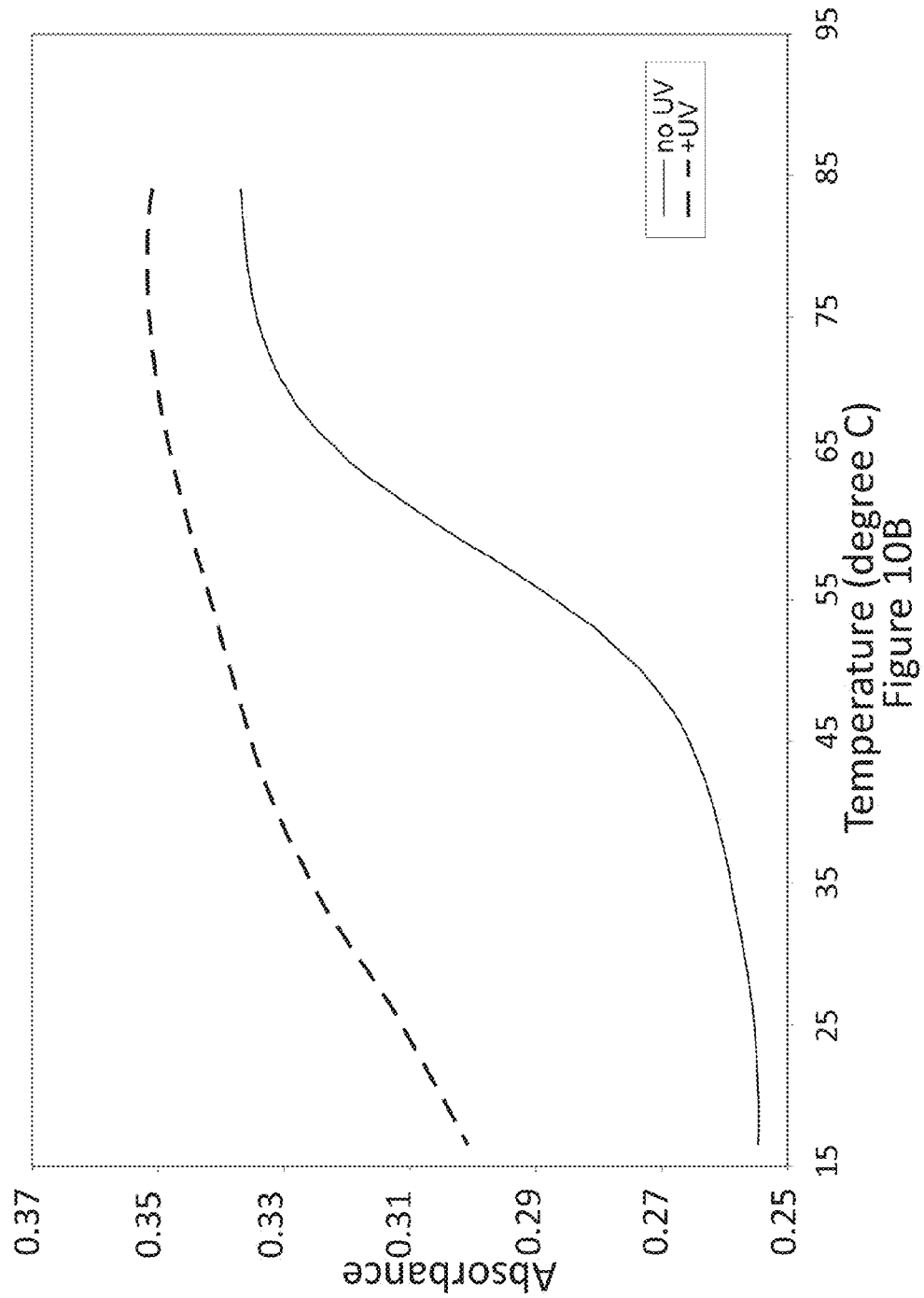

|  |  | wavelength | intensity | $I_a/(I_a+I_d)$ |
|---|---|---|---|---|
| Photolyzed | Cy3 | 564.0200195 | 176.3082528 | ($I_d$) |
|  | Cy5 | 666.9500122 | 8.543438911 | ($I_a$) |
|  |  |  |  | 0.046218 |
| Un-photolyzed | Cy3 | 565.0700073 | 17.26920915 | ($I_d$) |
|  | Cy5 | 667.9699707 | 35.86405182 | ($I_a$) |
|  |  |  |  | 0.674983 |

TRANSCRIPTOME IN VIVO ANALYSIS

CROSS-REFERENCE TO RELATED APPLICATIONS

The present application claims priority under 35 U.S.C. §119(e) to U.S. Provisional Patent Application No. 61/614,940, filed Mar. 23, 2012, and is a continuation-in-part of, and claims priority to U.S. patent application Ser. No. 13/702,415, filed Dec. 6, 2012, which is the U.S. national phase application filed under 35 U.S.C. §371 claiming benefit to International Patent Application No. PCT/US2011/039447, filed on Jun. 7, 2011, which is entitled to priority under 35 U.S.C. §119(e) to U.S. Provisional Patent Application No. 61/352,199, filed Jun. 7, 2010, each of which applications is hereby incorporated by reference in its entirety.

STATEMENT REGARDING FEDERALLY SPONSORED RESEARCH OR DEVELOPMENT

This invention was made with government support from the National Institute of Health, grant numbers GM083030, NIHAG9900 and DP1OD004117. The government has certain rights in the invention.

BACKGROUND OF THE INVENTION

Single cells are the building blocks upon which complex tissue and systems are developed. It is believed that a detailed molecular fingerprint of individual cells in the context of the other cells within the system would provide a blueprint for manipulation of the system in an effort to produce predictable outcomes. For example assessment of individual hippocampal neurons in context of the various interacting cells from normal and Alzheimer's brain promises to highlight systemic constraints and influences on cell functioning in the disease state.

It has been possible to isolate and analyze the mRNA complement from individual cells for several years, in particular with regard to dispersed cells in culture. This information is intriguing but lacks the "systemic" regulation component associated with the cell being in intact live tissue. The isolation of single cells from in vivo is compromised by the complex structure of intact tissues with many types of cells tightly intermingled with one another. A number of techniques, including in situ transcription, automated fluorescent cell sorting (FACS-array) and laser capture microdissection (LCM), have to date attempted to generate gene expression information from single cells or populations of cell in situ. However, their use is limited the investigation of RNA in vivo in combination with other in vivo techniques, such as live-imaging or electrophysiology, a combination that would provide reforming and novel insights into in vivo functioning.

There is a need in the art for a method to quantify gene expression in individual live cells from an intact functioning tissue or organism. The present invention satisfies this need.

SUMMARY OF THE INVENTION

The present invention provides compositions and methods for introducing a molecule into at least one cell such that when the molecule is activated in the at least one cell, or cellular compartment, the molecule captures RNA only in the at least one cell or cellular compartment where the molecule has been activated. Preferably, the activation of the molecule is spatially controlled. In one embodiment, the compositions and methods of the invention allow for the isolation of RNA in individual live cells.

In one embodiment, the invention is a hybrid nucleic acid molecule having a first, second, and third oligomer, where the first oligomer is linked to the second oligomer through a first photocleavable linker and the second oligomer is linked to the third oligomer through a second photocleavable linker. In some embodiments, the hybrid nucleic acid molecule of the invention further includes a label for isolating nucleic acids and a moiety comprising a cell penetrating domain (CPD).

In some embodiments, the hybrid nucleic acid molecule of the invention has a first oligomer that is at least an 18mer 2'-fluoro, a second oligomer that is at least a poly-A 7mer, and a third oligomer is at least a poly-A 7mer. In other embodiments, the hybrid nucleic acid molecule of the invention has a first oligomer that is at least an 18mer 2'-fluoro, a second oligomer that is at least a poly-A 7mer, and a third oligomer is at least a poly-A 14mer.

In one embodiment, the hybrid nucleic acid molecule of the invention is caged in the absence of cleavage of the photocleavable linker. In other embodiments, the hybrid nucleic acid molecule of the invention is uncaged in the presence of cleavage of the photocleavable linker.

In some embodiments, the label is a linked to the first oligomer. In certain embodiments, the label is biotin. In some embodiments, the CPD is linked to the third oligomer.

In one embodiment, the invention is a hybrid nucleic acid molecule having a first and second oligomer, where the first oligomer is linked to the second oligomer through a photocleavable linker. In some embodiments, the hybrid nucleic acid molecule of the invention further includes a label for isolating nucleic acids and a moiety comprising a cell penetrating domain (CPD).

In one embodiment, the hybrid nucleic acid molecule of the invention is caged in the absence of cleavage of the photocleavable linker. In other embodiments, the hybrid nucleic acid molecule of the invention is uncaged in the presence of cleavage of the photocleavable linker.

In some embodiments, the label is a linked to the first oligomer. In certain embodiments, the label is biotin. In some embodiments, the CPD is linked to the second oligomer.

In another embodiment, the invention is a method of isolating nuclear RNA from at least one live cell, the method including the steps of: 1) introducing a hybrid nucleic acid molecule of the invention into the nucleus of a cell, 2) activating the molecule in the nucleus under conditions suitable for binding of the nucleic acid portion of the hybrid molecule to cellular RNA, where the activation cleaves the photocleavable linkers in the molecule, 3) allowing the formation of a hybridized nucleic acid molecule/nuclear RNA complex, and 4) isolating the hybridized nucleic acid molecule/nuclear RNA complex. The introduced hybrid nucleic acid molecule has a first, second, and third oligomer, where the first oligomer is linked to the second oligomer through a first photocleavable linker and the second oligomer is linked to the third oligomer through a second photocleavable linker. In some embodiments, the hybrid nucleic acid molecule further includes a label for isolating nucleic acids and a moiety comprising a cell penetrating domain (CPD).

In some embodiments, the hybrid nucleic acid molecule has a first oligomer that is at least an 18mer 2'-fluoro, a second oligomer that is at least a poly-A 7mer, and a third oligomer is at least a poly-A 7mer. In other embodiments, the hybrid nucleic acid molecule of the invention has a first oligomer that is at least an 18mer 2'-fluoro, a second oligomer that is at least a poly-A 7mer, and a third oligomer is at least a poly-A 14mer.

In one embodiment, the hybrid nucleic acid molecule is caged in the absence of cleavage of the photocleavable linker. In other embodiments, the hybrid nucleic acid molecule of the invention is uncaged in the presence of cleavage of the photocleavable linker.

In some embodiments, the label is a linked to the first oligomer. In certain embodiments, the label is biotin. In some embodiments, the CPD is linked to the third oligomer.

In one embodiment, the molecule is activated by cleavage of the photocleavable linker. In one embodiment, cleavage of the photocleavable linker comprises administering ultraviolet light to the nucleus. In one embodiment, cleavage of the photocleavable linker comprises administering light to the nucleus, wherein the light has a wavelength of about 350-1500 nm. In another embodiment, cleavage of the photocleavable linker comprises exposing the nucleus to two photon excitation of near-infrared or infrared light.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A and 2B, is a series of images depicting the synthesis of the TIVA-tag. FIG. 2A depicts structures of 2'-Fluoro TIVA-tag without Cy3/Cy5 dyes. FIG. 2B depicts structures of 2'-Fluoro TIVA-tag with Cy3/Cy5 dyes.

FIG. 4, comprising FIG. 4A shows TIVA-tags without Cy3/Cy5 dyes. Melting temperature before photolysis was 55.8° C., while after photolysis it was 31.1° C. FIG. 4B shows TIVA-tags with Cy3/Cy5 dyes. Melting temperature before photolysis was 58.9° C.; Melting temperature after photolysis was 29.0° C.

FIGS. 5A and 5B, is a series of images depicting wavelength parameters for TIVA-tag. FIG. 5A is an image depicting wavelength scan of Cy3/Cy5 labeled TIVA-tag excited at 552 nm, before and after photolysis. FIG. 5B is an image depicting intensities at different emission wavelengths and the ratio of acceptor Cy5 intensity divided by the total intensity of Cy3 and Cy5 emission.

FIGS. 7A and 7B, is a series of images depicting results from bioanalyzer experiments. FIG. 7A demonstrates that amplified RNA (aRNA) abundance parallels the amount of TIVA-tag given to the neuronal cells. FIG. 7B depicts size distribution of RNA isolated from neurons after TIVA-tag administration and photocleavage.

FIG. 9, comprising

FIG. 10, comprising FIGS. 10A and 10B, is a series of images depicting melting curves. FIG. 10A depicts 2'-fluoro TIVA-tag without Cy3/Cy5 dyes. Melting temperature before photolysis (solid line) was 56° C., and melting temperature after photolysis (broken line) was 31° C. FIG. 10B depicts 2'-fluoro TIVA-tag with Cy3/Cy5 dyes. Melting temperature before photolysis (solid line) was 59° C., melting temperature after photolysis (broken line) was 29° C.

FIG. 11, comprising

DETAILED DESCRIPTION OF THE INVENTION

The invention described herein arises from the discovery that a molecule can be introduced into a cell such that, when the molecule is activated in the cell, the molecule captures the RNA only in the cell in which the molecule has been activated. In one embodiment, the invention provides compositions and methods that permit the molecule to enter a cell and when specifically activated within the cell, the molecule anneals to the endogenous cellular RNA and permits the isolation of the RNA.

In one embodiment, the invention provides compositions and methods that permit the molecule to enter a subcellular compartment and when the molecule is specifically activated within the subcellular compartment, the molecule anneals to the endogenous RNA of the compartment and permits the isolation of the RNA. In another embodiment, the invention provides compositions and methods that permit the molecule to enter the nucleus of the cell and when the molecule is specifically activated within the nucleus, the molecule anneals to the endogenous RNA in the nucleus and permits the isolation of the RNA.

In one embodiment, the molecule of the invention can be used to isolate RNA from a cell in any environment. For example, the cell can be in culture, in live tissue slices, or in intact animal. In one embodiment, the molecule of the invention can be used to isolate RNA from cellular subregions such as dendrites or axons that are in contact with other cells. In yet another embodiment, the molecule of the invention can be used to isolate RNA from individual neoplastic cells in a tissue or tumor.

In one embodiment, the molecule of the invention can be used to isolate RNA from single cells with high spatial and temporal resolution.

In one embodiment, the molecule of the invention is an antisense strand that is conjugated via a photocleavable linker to a blocking strand. Upon photolysis, the blocking strand dissociates from the antisense strand, thereby allowing the antisense strand to bind to a target nucleotide.

Figure 8:
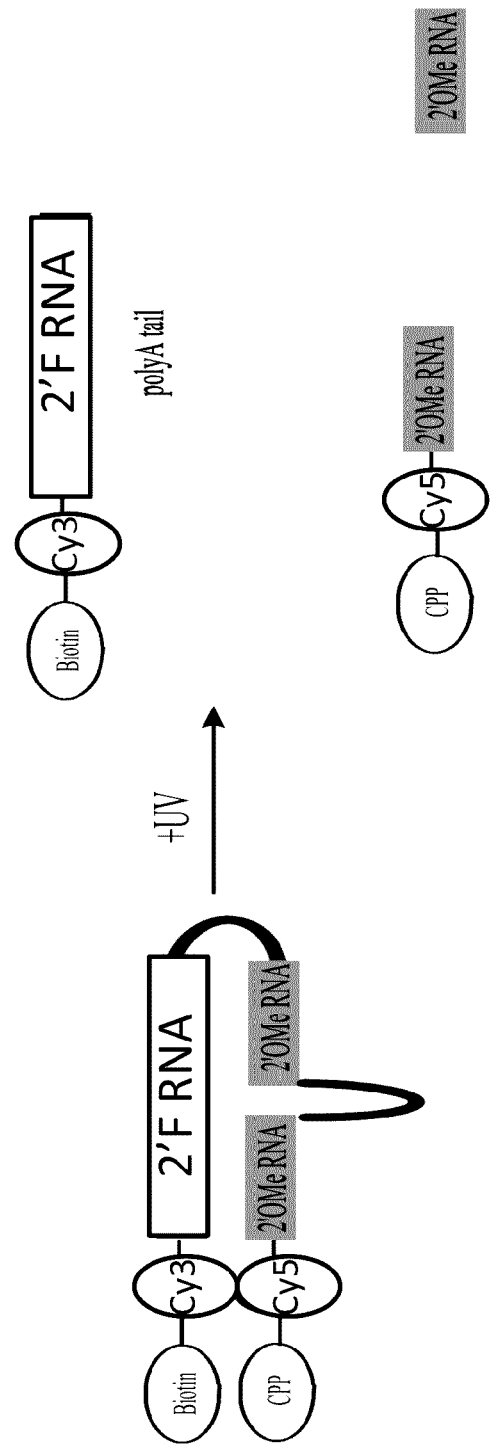
FIG. 8 is a schematic of caged 2'-fluoro RNA strand which is caged via a photocleavable linker to two shorter complementary 2'-OMe RNA strands that are joined by a second photocleavable linker. The 2'-fluoro RNA strand is tagged with a biotin moiety and the cell-penetrating peptide (CPP) is connected through a disulfide bond to the 5' end of the 2'-OMe RNA strand. Upon photolysis, the complementary strand breaks into two shorter oligonucleotides and dissociates. Dissociation can be monitored using a Cy3 on the 2'-fluoro RNA and Cy5 on the 2'-OMe RNA. The 2'-fluoro RNA can then hybridize to the polyA tail of the mRNA in the cell.

In one embodiment, the molecule of the invention is an antisense strand that is conjugated via a photocleavable linker to a blocking strand that itself is divided into one, two or more parts, each separated by a photocleavable linker (see e.g. FIG. 8). Upon photolysis, the blocking strand breaks into two much shorter oligonucleotides that dissociate from the antisense strand allowing the blocking strand to be as long as possible before photolysis in order to block the antisense oligonucleotide from binding its normal RNA target.

In one embodiment, the invention provides compositions and methods for introducing a caged molecule into a population of cells and then uncaging the molecule in at least one cell in order to isolate RNA from the at least one cell. In some instances, the caged molecule refers to the inactivated molecule and the uncaged molecule refers to the activated molecule.

In one embodiment, the invention provides a method of isolating RNA in a cell by introducing the molecule of the invention into the recipient cell. In a preferred embodiment, the method is termed Transcriptome In Vivo Analysis (TIVA) methodology. In the TIVA methodology, a hybrid nucleic acid molecule is synthesized, with functional groups that enable the molecule to enter at least one specific, selected or desired target cell, where when specifically activated within at least one cell, cell nucleus, or subcellular compartment, the molecule anneals to the endogenous cellular RNA and permits isolation of the RNA. Accordingly, the molecule of the invention sometimes is referred to as TIVA-tag.

In one embodiment, the hybrid nucleic acid molecule of the invention permits isolation of cellular RNA by way of a label. In one aspect of the invention, a label for isolating cellular RNA is selected from the group consisting of biotin, dinitrophenyl, acridine, digoxigenin, c-myc, His-tag, fluorescein, rhodamine, cyanine, digoxigenin, an intercalator, a minor-groove binder, a chemiluminescent precursor, selenium and cadmium. However, the invention should not be limited to any particular label. This is because a skilled artisan would recognize the applicability of any suitable label in the context of the hybrid nucleic acid molecule of the invention for isolating a nucleic acid complex.

In one embodiment, the structure of TIVA-tag comprises the following functional groups: 1) a poly 2'-fluoro-TTP (2FRNA); 2) a cell penetrating domain (CPD); 3) a photocleavable linker; and 4) a biotin molecule. In another embodiment, the structure of TIVA-tag comprises the following functional groups: 1) a poly 2'-fluoro-TTP (2FRNA); 2) a cell penetrating domain (CPD); 3) a photocleavable linker; 4) a biotin molecule; 5) a disulfide bond; and 6) a fluorescing FRET pair.

In one embodiment, the CPD is a domain that allows penetration of the TIVA-tag into a cell. In one embodiment, the CPD is cell specific, thereby allowing entry of the TIVA-tag in only a particular cell population. In one embodiment, the CPD allows entry of the TIVA-tag in all cells. It should be understood that when certain methods of introduction are employed, a CPD is not necessary and may be excluded from the TIVA-tag. For example, in certain embodiments, the TIVA-tag is introduced into a cell without the use of a CPD. Rather, in certain embodiments the TIVA-tag is introduced into the cell using known transfection techniques. In some embodiments, the CPD is a cell-penetrating peptide (CPP). In other embodiments, the CPD is not a peptide (e.g., folate).

In one embodiment, the TIVA-tag comprises an antisense oligonucleotide that can hybridize to the desired cellular RNA target. In yet another embodiment, the TIVA-tag comprises a 2'-fluoro RNA antisense strand that further comprises a photocleavable spacer joined to a blocking strand, a biotin tag, and a 5' thiol. The blocking strand is comprised of 2'-OMe RNA, which increases thermal stability and nuclease resistance of the molecule. The biotin tag allows the antisense strand bound to cellular mRNA to be isolated easily using, by way of examples, magnetic beads or beads conjugated to a biotin-binding moiety such as streptavidin, avidin or anti-biotin antibodies. The 5' thiol is installed to allow conjugation of the molecule, in some embodiments, to a cell-penetrating domain (CPD). In some instances, a FRET pair is incorporated at the 3' end of the antisense strand and the 5' end of the blocking strand. This allows for monitoring the dissociation of the two strands upon photolysis.

In one embodiment, the molecule of the invention comprises a 2'-fluoro RNA designed to bind the polyA tails of all mRNAs in a photolyzed cell and, after lysis, the hybridized 2'-fluoro RNA/mRNA can be affinity-purified by magnetic beads. In various embodiments, the mRNA is dissociated from the 2'-fluoro RNA by heating or changing the salt concentration or combinations thereof. Then, the recovered mRNA and the transcript are amplified to determine what is present in the cell. Caging these 2'-fluoro oligonucleotides allow them to be uncaged in single cells, and the RNA population from that one cell can be identified.

In one embodiment, the molecule of the invention comprises: a) a first, second, and a third oligomer, wherein the first oligomer is linked to the second oligomer through a first photocleavable linker; b) a label for isolating nucleic acids; and, optionally, c) a CPD.

In another embodiment, the molecule of the invention comprises: a) a first, second, and third oligomer, wherein the first oligomer is linked to the second oligomer through a first photocleavable linker and the second oligomer is linked to the third oligomer through a second photocleavable linker; b) a label for isolating nucleic acids; and, optionally, c) a CPD.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Amplification" refers to any means by which a polynucleotide sequence is copied and thus expanded into a larger number of polynucleotide molecules, e.g., by reverse transcription, polymerase chain reaction, and ligase chain reaction, among other methods.

"Antisense" refers to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Binding" is used herein to mean that a first moiety interacts with a second moiety.

"Biological sample," as that term is used herein, means a sample obtained from a single-cellular or multi-cellular organism that can be used to assess the level of expression of a nucleic acid, the level of a protein present, or both. Such a sample includes, but is not limited to, a cell, a blood sample, a neural tissue sample, a brain sample, and a cerebrospinal fluid sample.

"Caged" is used herein to describe a molecule that is in an inactive state. For example, in certain embodiments, a caged molecule has a conformation that prevents the activity of the molecule. In contrast, an "uncaged" molecule describes a molecule in an active state. In certain embodiments, an uncaged molecule has a conformation that allows the activity of the molecule. In certain embodiments, an uncaged molecule is generated from a corresponding caged molecule. For example, in one embodiment, a caged molecule is activated to become an uncaged molecule.

A "cell penetrating domain" is used herein to refer to a domain that facilitates the entry of said domain, along with any molecule associated with the domain, across one or more membranes to the interior of a cell.

A "cell penetrating peptide" is used herein to refer to a polypeptide that facilitates the entry of said polypeptide, along with any molecule associated with the polypeptide, across one or more membranes to the interior of a cell.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "fluid medium" or "fluid media" is used herein to refer to a form of matter, such as air, liquid, solid or plasma, preferably liquid, that is capable of flowing.

An "isolated cell" refers to a cell which has been separated from other components and/or cells which naturally accompany the isolated cell in a tissue or organism.

An "isolated nucleic acid" refers to a nucleic acid (or a segment or fragment thereof) which has been separated from sequences which flank it in a naturally occurring state, e.g., a RNA fragment which has been removed from the sequences which are normally adjacent to the fragment. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Linker" refers to one or more atoms comprising a chain connecting a nucleic acid analog to a moiety such as a peptide, nucleotide, label, modifier, stabilizing group, or the like.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

"Nucleic acid analogs" are structurally modified, polymeric analogs of DNA and RNA made by chemical synthesis from monomeric nucleotide analog units, and possessing some of the qualities and properties associated with nucleic acids. PNA and phosphorothioate oligonucleotides are examples of two of many nucleic acid analogs known in the art. "Watson/Crick base-pairing" and "Watson/Crick complementarity" refer to the pattern of specific pairs of nucleotides, and analogs thereof, that bind together through hydrogen bonds, e.g. A pairs with T and U, and G pairs with C. The act of specific base-pairing is "hybridization" or "hybridizing". A hybrid forms when two, or more, complementary strands of nucleic acids or nucleic acid analogs undergo base-pairing.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "photoreactive label" refers to a label that becomes chemically active upon irradiation of the label with light energy. Light energy useful for activating such labels includes, but is not limited to, visible light, ultraviolet (UV) light, infrared (IR) light, among others. An activated label may contain a free radical, or other highly reactive group, and may be reactive with an adjacent molecule. By way of a non-limiting example, para-benzoylphenylalanine (BPA) is a photoreactive amino acid that may be incorporated into a peptide. Activation of BPA with UV light causes the benzoyl moiety of the amino acid to be released, leaving a phenylalanine residue containing a free radical, which is available to crosslink with other amino acids and/or proteins within proximity.

A photoreactive label is "incorporated into" a nucleic acid analog or a cell-penetrating peptide when the label is attached to, incorporated within, integrated into, or linked to the nucleic acid analog or the cell-penetrating peptide. This includes coupling of a label to the terminus of a nucleic acid analog or a cell-penetrating peptide as well as incorporating the label into a nucleic acid analog or a cell-penetrating peptide by including a nucleobase or amino acid analog that contains such a label.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As applied to a protein, a "fragment" of a polypeptide, protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length, and any and all integers there between.

A "genomic DNA" is a DNA strand which has a nucleotide sequence homologous with a gene as it exists in the natural host. By way of example, a fragment of a chromosome is a genomic DNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

"Conjugate" or "conjugated" refer to a covalent, ionic, or hydrophobic interaction whereby the moieties of a molecule are held together and preserved in proximity.

"Chimera" as used herein refers to an oligonucleotide including one or more nucleotide and one or more nucleotide analog units. The monomer units are linked through phosphodiester and phosphodiester analog linkages.

"Phosphodiester analog" or "internucleotide analog" refer to analogs of natural phosphodiester 3',5'-internucleotide linkages differing in their composition and/or location of attachment to a nucleotide, including but not limited to 2',5'-linkage, 3',3'-linkage, 5',5' linkage, methyl phosphonate, alkylated phosphotriester, 3'-N-phosphoramidate, and non-bridging N-substituted phosphoramidate.

The term "2'-modified RNA" means a nucleic acid analog containing one or more ribonucleotides in which a 2' position on a sugar bears a substituent replacing a hydroxyl. As an example, 2'-O-alkyl RNA comprises a nucleic acid analog containing one or more ribonucleotides in which a 2' position on a sugar consists of the moiety —OR where R is lower alkyl, such as, but not limited to, a methyl or ethyl moiety (Sproat, 1994, Protocols for Oligonucleotides and Analogs, Humana Press).

The terms "permeant" and "permeable" refer to the ability of a construct of the present invention to pass through a cellular membrane, a cell compartment membrane, or a nuclear membrane, or ascribed as characteristics of the susceptibility of membranes to have constructs pass through them (Alberts et al., 1989, Molecular Biology of the Cell, 2nd Ed., Garland Publishing, New York).

"Detection" refers to detecting, observing, or measuring a construct on the basis of the properties of a detection label.

The term "labile" refers to a bond or bonds in a molecule with the potentiality of being cleaved by reagents, enzymes, or constituents of a cell.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. It is understood that any and all whole or partial integers between any ranges set forth herein are included herein.

DESCRIPTION

The present invention provides compositions and methods for introducing a molecule into at least one cell such that when the molecule is activated in the at least one cell, the molecule captures cellular RNA only in the at least one cell where the molecule has been activated. Preferably, the activation of the molecule is spatially controlled. In one embodiment, the compositions and methods of the invention allows for the isolation of RNA in individual live cells.

Compositions

The invention comprises a molecule that hybridizes with an intracellular polynucleotide. The molecule of the invention is a hybrid nucleic acid molecule comprising functional groups that enable the molecule to enter a cell in an inactive form and when activated within a single cell or subcellular compartment, the molecule binds to endogenous cellular RNA and therefore permits the isolation of the cellular RNA.

The invention features a hybrid nucleic acid molecule wherein the nucleic acid portion is able to hybridize to the target polynucleotide (e.g., cellular RNA). In one embodiment, the nucleic acid portion of the hybrid molecule of the invention hybridizes to poly A tails of cellular RNA when the hybrid molecule is activated within the cell. In this way, the nucleic acid portion is an antisense molecule with respect to cellular poly A tails. In another embodiment, the nucleic acid portion of the hybrid molecule has a sequence that hybridizes to specific nucleic acid sequences. Thus, in one embodiment, the sequence of the nucleic acid portion of the hybrid molecule is designed to target a specific polynucleotide species. In one embodiment, the targeted specific polynucleotide species has a sequence that deviates from a wild-type sequence (e.g., a gene mutation, single nucleotide polymorphism, etc.). The nucleic acid portion of the hybrid molecule is therefore not limited to any particular sequence. The sequence of the nucleic acid portion may be of any sequence that directs the hybridization of the nucleic acid portion to any desired target polynucleotide or to any collection of desired target polynucleotides. The target polynucleotide may be any type of polynucleotide or nucleic acid. For example, in certain embodiments, the target polynucleotide is cellular RNA. For example, the target polynucleotide can include, but is not limited to, messenger RNA (mRNA), cDNA, genomic DNA, fragmented RNA, fragmented DNA, intronic RNA, exonic RNA, microRNA, and the like.

In another embodiment of the present invention, the nucleic acid molecule portion of the hybrid molecule is a nucleic acid analog, preferably is a modified sugar analog. In one aspect, a sugar moiety of at least one of the nucleotides of a nucleic acid analog is modified. In one embodiment, the 2'-position of a nucleoside is modified. Oligonucleotides bearing 2'-modified nucleosides have been studied as ribozymes, nuclease-resistance antisense analogs, and other cellular mechanism probes (Lamond, A., et al., Cell, 58:383-90 (1989); (Goodchild, J., Nucleic Acids Research, 20:4607-12 (1992)). Desirable features of 2'-O-alkyl-oligoribonucleosides include high chemical stability, substantial RNA- and DNA-nuclease resistance (including RNaseH), and increased thermal duplex stability (Ohtsuka, E., et al., U.S. Pat. No. 5,013,830, issued May 7, 1991)

In another embodiment, a fraction of the ribonucleotides of a nucleic acid analog are 2'-O-alkylribonucleotides, preferably 2'-O-methyl-ribonucleotides. Additional preferred modified ribonucleotides include 2'-O-allyl-ribonucleotides, ribonucleotides, 2'-halo-ribonucleotides, 2'-O-methoxyethyl-ribonucleotides, 2'-branching group-ribonucleotides, and 2'-O-branching group-ribonucleotides. Preferably, the invention features a hybrid nucleic acid molecule wherein the nucleic acid portion is 2' fluoro RNA.

In addition to the 2'-fluoro RNA antisense strand, the hybrid nucleic acid molecule further comprises a photocleavable spacer joined to a blocking strand, which in turn is linked to a 3' biotin tag, and a 5' thiol. In some instances, the blocking strand comprises of 2'-OMe RNA, which serves to increase thermal stability and nuclease resistance of the molecule. The 3' biotin tag allows the antisense strand that is bound to cellular mRNA to be isolated.

In one embodiment, the hybrid molecule of the invention comprises an antisense strand linked to a blocking strand through a first photocleavable linker. As would be understood by those skilled in the art, the antisense strand of the invention is of any suitable length necessary to bind to a target nucleotide. In certain embodiments, the antisense strand is a nucleotide oligomer comprising 1 or more, 2 or more, 5 or more, 10 or more, 15 or more, 20 or more, 30, or more, or 50 or more nucleotide bases.

Further, the blocking strand of the invention is of any suitable length to hybridize to the antisense strand. In certain embodiments, the antisense strand is a nucleotide oligomer comprising 1 or more, 2 or more, 5 or more, 10 or more, 15 or more, 20 or more, 30, or more, 50 or more, or 100 or more nucleotide bases.

In certain embodiments, the hybrid molecule of the invention comprises a first and second oligomer, wherein the first oligomer is linked to the second oligomer through a first photocleavable linker. For example, in one embodiment, the first oligomer is the antisense strand. In one embodiment, the second oligomer is the blocking strand.

In certain embodiments, the blocking strand is divided into one, two or more parts, each separated by a photocleavable linker. Each portion of the divided blocking strand is of any suitable length. In certain embodiments, each portion of the divided blocking strand is a nucleotide oligomer comprising 1 or more, 2 or more, 5 or more, 10 or more, 15 or more, 20 or more, 30, or more, 50 or more, or 100 or more nucleotide bases.

In certain embodiments, the hybrid molecule of the invention comprises a first, second, and third oligomer, wherein the first oligomer is linked to the second oligomer through a first photocleavable linker and the second oligomer is linked to the third oligomer through a second photocleavable linker. For example, in one embodiment, the first oligomer is the antisense strand. In one embodiment, the second and third oligomer combine to form the blocking strand.

In another embodiment of the invention, at least two of the nucleotides making up the nucleic acid analog moiety are linked through nonstandard internucleotide linkages. By way of a non-limiting example, nonstandard internucleotide linkages include 2'-5'-linkages, inverted 3'-3' and 5'-5' linkages, methyl phosphonate, non-bridging N-substituted phosphoramidate, alkylated phosphotriester branched structures, 3'-N-phosphoramidate, peptide nucleic acid (PNA), and a non-nucleosidic polymer, among others. The term "non-nucleosidic polymer" refers to a polymer which is not a polynucleotide, e.g., polyethylene oxide, polypeptide, polyacrylamide, and polycarbohydrate.

In yet another embodiment of the present invention, at least one of the nucleotides in the nucleic acid analogs include modified nucleobases. Nucleobase modifications of the invention include, but are not limited to, C-5-alkyl pyrimidine, 2,6-diaminopurine, 2-thiopyrimidine, C-5-propyne pyrimidine, 7-deazapurine, isocytosine and isoguanine, and universal base, which shows diminished base-specific discrimination in a Watson/Crick, base-pairing hybridization interaction, e.g., 3-nitropyrrole (Nichols, R., et al., Nature, 369:492-3 (1994)) and 5-nitroindole (Loakes, D., et al., Nucleic Acids Research, 22:4039-43 (1994)).

Generally, the design and synthesis of a nucleic acid analog of the invention follows conventional teachings. By way of a non-limiting example, a nucleic acid analog is synthesized on an automated, solid-phase DNA synthesizer using phosphoramidite chemistry (Beaucage, S. L., et al., Tetrahedron, 48:2223-2311 (1992)); (Caruthers, M., et al., U.S. Pat. No. 4,415,732, issued Nov. 15, 1983); e.g. ABI 392 or 394 DNA synthesizer (PE Applied Biosystems, Foster City, Calif.), or on an automated, solid-phase peptide synthesizer, e.g. ABI 433 Peptide synthesizer (PE Applied Biosystems, Foster City, Calif.).

Nucleic acid analogs of the invention are generally synthesized using known synthetic techniques. The chemistry used to form polynucleotides is well known in the art, and can be found in such references as Beaucage, 1992, supra. The phosphoramidite method of polynucleotide synthesis for making the nucleic acid analogs of the invention is a preferred method because of its efficient and rapid coupling and the stability of the starting nucleoside monomers. The synthesis is typically performed with the growing polymer chain attached to a solid support, so that excess reagents, which are in the liquid phase, can be easily removed by filtration, thereby eliminating the need for purification steps between cycles (Caruthers, M., et al., U.S. Pat. No. 4,458,066, issued Jul. 3, 1984).

The 5' thiol allows conjugation of the molecule, in certain embodiments, to a cell-penetrating domain (CPD). As will be understood by one of skill in the art, a CPD has the ability to permeate a cell membrane, or be transported across a cell membrane. In some embodiments, a CPD has the ability to permeate a nuclear membrane, or be transported across a nuclear membrane. Further, as described elsewhere herein, a CPD has the ability to carry a cargo across a cell membrane. Examples of cargo include, but are not limited to, a peptide, a nucleic acid, and a photoreactive label. Other properties of CPDs include, but are not limited to, the ability to induce endocytosis of a cargo into a cell.

The skilled artisan, when armed with the disclosure set forth herein, will know how to identify a CPD useful in the present invention. Briefly, a CPD useful in the present invention is one that can form a membrane-permeable construct when coupled with a nucleic acid analog of the invention. That is, any CPD that confers the property of membrane permeability upon a CPD-nucleic acid analog construct is encompassed by the present invention. A CPD useful in the present invention can be any natural or synthetic compound found in the art. For example, a CPD useful in the present invention includes, but is not limited to, nucleic acids, peptides, proteins, small molecules, polysaccharides, organic compounds, and inorganic compounds.

However, a CPD useful in the present invention should not be limited to those disclosed herein. Rather, the skilled artisan, when armed with the present disclosure, will understand that any CPD that can transport a nucleic acid analog into a cell, known now or yet to be discovered, should be construed to be encompassed by the present invention.

In one embodiment, the CPD is folate. In another embodiment, a CPD is a cell penetrating peptide (CPP). The extensive disclosure provided in U.S. Patent Application Publication Nos. 20080199854 and 20100041025 directed to CPP are incorporated by reference as if set forth in their entirety herein. For example, the CPP can comprise an amino acid sequence that confers cell-penetrating properties upon the CPP.

The present invention also provides analogs of proteins or peptides which comprise a CPP as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are a CPP which has been altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a CPP of the present invention. For example, a derivative of the CPP transportan may have one or more additional amino acids added to either end of the peptide. Such biological/biochemical properties include, but are not limited to, the transport of a cargo across a cell membrane.

In one embodiment, the CPD of the molecule allows entry of the molecule into a target cell population. This target cell population can be defined by its cell type, age, metabolic activity, specific protein expression, specific receptor expression, and the like. For example, in one embodiment, the CPD is designed to target entry of the TIVA-tag specifically into cells expressing a particular receptor. For example, in one embodiment, the CPD is folate. In one embodiment, a TIVA-tag wherein the CPD is folate (Folate TIVA-tag) binds to a folate receptor (FR) on a cell that expresses FR on the cell surface. Other non-limiting examples of cell surface receptors in which the molecule can be directed to enter a target cell population include HER2, EGFR, transferrin receptor, chemokine receptor, asialoglycoprotein receptor, TrkA, and p75NTR. In one embodiment, the identity of the CPD directs the molecule to a target cell population. Non-limiting examples of CPDs used to direct the molecule to a target cell population include folate, EGF, transferrin, NGF, chemokines, asialoglycoprotein, riboflavin, RGD sequence, ICAM-1 antibody, LDL, cholera toxin B, Mannose-6-phosphate, nicotinic acid, or portions thereof. In some embodiments, the target cell expressing a particular cell surface receptor is a tumor cell. In some embodiments, the CPD of the molecule allows entry of the molecule into any cell type. Thus, in certain embodiments, the molecule of the invention is not targeted to any particular cell type.

In one embodiment, the molecule of the invention enters and may be activated in a subcellular compartment of a cell. Activation of the molecule in a subcellular compartment can be achieved by focusing the activating laser with sufficient resolution to irradiate only the desired compartment of the cell. Activation of the molecule in the subcellular compartment allows isolation of polynucleotides in that compartment. Non-limiting subcellular compartments where the molecule can enter and be activated include the nucleus, nucleosome, mitochondria, chloroplast, dendrite, soma, and lysosome. In one embodiment, the CPD is directed to distinct subcellular sites. For example, in certain embodiments, the CPD can include a nuclear localization sequence to allow entry of the molecule to the nucleus. In another embodiment, the molecule enters a subcellular compartment, for example the nucleus, independent of the CPD. For example, in certain embodiments the CPD does not specifically direct the molecule into any compartment; rather the molecule enters the compartment through other mechanisms. In one embodiment, activation of the molecule in the nucleus (TIVA-nuc) allows hybridization and enrichment of newly transcribed mRNA transcripts.

In one embodiment, a FRET pair can be incorporated at the 3' end of the antisense strand and the 5' end of the blocking strand. A FRET pair allows for monitoring the dissociation of the two strands of the molecule of the invention upon photolysis. A non-limiting example of a FRET pair is the Cy3/Cy5 fluorophores.

The present invention also includes peptides to which one or more labels have been added. A label may be used for the identification and/or purification of the peptide, or for the identification of the biological role or biological interactions of the peptide. A label useful in the present invention should have a unique or identifiable property, such as fluorecence, radioactive signal, light emission, phosphorescence, paramagnetism, and the like, which may be detectable using any spectroscopic or spectrophotometric technique known in the art. Protein labels useful in the present invention includes, but should not be limited to, biotin, dinitrophenyl, acridine, fluorescein, rhodamine, cyanine (such as Cy3 and Cy5, among others), digoxigenin, an intercalator, a minor-groove binder, a chemiluminescent precursor, selenium, cadmium, labels useful in quantum dot technology, and the like.

In one embodiment, the 2'-fluoro RNA is designed to bind the polyA tails of all mRNAs in a photolyzed cell and, after lysis, the hybridized 2'-fluoro RNA/mRNA can be isolated using standard techniques such as being affinity-purified using magnetic streptavidin beads.

The general conjugation strategy to prepare the hybrid nucleic acid molecule of the invention is to synthesize the nucleic acid analog and the other moieties separately. Reagents and automated synthesizers are commercially available for the synthesis of nucleic acid analogs. Each moiety can be further derivatized to contain reactive functionality to form a linkage. Nucleic acid analogs can be covalently coupled to peptides through any suitable bond. In one embodiment of the invention, suitable bonds include labile bonds, such as a disulfide. To form a disulfide bond in a construct between the nucleic acid analog and peptide, the two moieties may be derivatized to contain thiol groups, one of which can contain a leaving group. In another embodiment of the invention, a linkage may be formed between a nucleic acid analog and a peptide using avidin-biotin chemistry. Methods of coupling avidin and biotin to a nucleic acid analog and a peptide are well-known in the art and will not be discussed herein.

Labile linkers allow degradation of the CPD-nucleic acid analog construct, which may be important under some conditions for reduction of unwanted effects, or for optimization of the function of the nucleic acid analog. For intracellular delivery, various labile linkers can be used. By way of a non-limiting example, disulfide bridges, pH sensitive linkers and protease/nuclease substrates can be used. The intracellular milieu is highly reductive in chemical potential, due to high (mM range) concentration of gluthathione. Thiol-containing gluthathione can exist in oxidized (disulfide) or reduced (thiol) form, the ratio of which is regulated by the enzyme glutathione-S-transferase, as well as other oxidative species. Compounds containing a disulfide bond undergo reaction with reduced gluthathione, leading to a reduced disulfide bond and oxidized gluthathione. For disulfide-containing CPD conjugates, the process has been characterized by Hällbrink et al (2001, Biochim Biophys Acta. 1515:101-9).

Methods

The present invention also provides methods of identifying RNA in an individual live cell. The method includes the steps of providing a hybrid nucleic acid molecule of the invention in an inactive form into a cell, activating the hybrid molecule in the cell under conditions suitable for binding of the nucleic acid portion of the hybrid molecule to cellular RNA, isolating the hybridized nucleic acid molecule/cellular RNA complex.

In one embodiment of the invention, the method includes lysing the cell containing the hybridized nucleic acid molecule/cellular RNA complex to form a cell lysate, contacting the cell lysate with a solid support conditions suitable to allow the hybridized nucleic acid molecule/cellular RNA complex to bind to the solid support to form a complex, and separating the complex from the lysate. In one aspect, the isolating step includes lysing the cell containing the hybridized nucleic acid molecule/cellular RNA complex to form a cell lysate, and contacting the cell lysate with a solid support comprising a binding moiety specific for a tag associated with the hybrid nucleic acid molecule of the invention. For example, if the tag is biotin, a binding moiety specific for the tag would be streptavidin beads. However, the invention should not be limited to biotin as the tag and streptavidin as the binding moiety thereof. Rather, the invention encompasses the used of any tag and corresponding binding moiety for purposes of isolating the hybridized nucleic acid molecule/cellular RNA complex from a cell or cell lysate.

The recipient cell for the hybrid nucleic acid molecule of the invention may be at least one of any type of cell. A recipient cell may be a eukaryotic cell or a prokaryotic cell. When the cell is a eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell, the cell is a bacterial cell. A recipient cell may be a differentiated cell and/or a non-dividing cell. The cell may also be a progenitor cell or a stem cell. Preferably, the recipient cell is a tissue-specific cell, more preferably a mammalian tissue-specific cell and more preferably still, a human tissue-specific cell. Non-limiting examples of cells suitable as a recipient cell include epithelial cells, neurons, fibroblasts, embryonic fibroblasts, keratinocytes, adult stem cells, embryonic stem cells, and cardiomyocytes.

The method of the invention may be carried on a cell comprising a cellular process. Such a cellular process includes, but is not limited to, a dendrite, an axon, a microvilli, a cilia, a stereocilia, a process, an astrocytic process, and the like.

The present invention further comprises methods for introducing the hybrid nucleic acid molecule of the invention into a live slice of tissue or a live animal. Methods for sustaining the cellular processes in the cells comprising a live slice of tissue are known in the art. As a non-limiting example, live slices can be refrigerated and perfused with natural or artificial fluids, such as artificial spinal fluid, artificial central nervous system fluid, and buffers disclosed elsewhere herein. Methods for the manipulation of live slice cultures are described in, for example, Roelandse, et al. (2004, J. Neuroscience, 24: 7843-7847); and Chen, et al. (2005, Magn. Reson. Med. 53: 69-75).

The methods disclosed herein comprise introducing the hybrid nucleic acid molecule of the invention to a cell that optionally comprises a cellular process, preferably a neuron comprising a dendrite, and isolating RNA from individual live cells. In one embodiment, the hybrid nucleic acid molecule of the invention is introduced to a subcellular compartment. Following introducing the hybrid nucleic acid-peptide molecule of the invention into a cell or compartment of interest, the cell or compartment is then exposed to an environment that activates the hybrid nucleic acid molecule of the invention. In one embodiment, activation of the hybrid nucleic acid molecule of the invention in a cell is accomplished by photolysis. For example, exposure to light induces cleavage of the photocleavable linker contained in the hybrid nucleic acid molecule of the invention. In one embodiment, the light is light from a laser source. In certain embodiments, the light is UV-light, visible light, near infrared light, or infrared light. In one embodiment, the light used to cleave the linker has a wavelength of about 350 nmm to about 1500 nm. In one embodiment, the photocleavable linker is designed to be cleaved when exposed to light of a particular wavelength, or range of wavelength. Once the photocleavable linker is disrupted from the hybrid nucleic acid molecule of the invention, the nucleic acid portion of the hybrid nucleic acid molecule of the invention is available for binding to target cellular RNA. For example, following photolysis, the 2'-fluoro RNA strand containing poly T's is available for binding to cellular poly A tails.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Synthesis of the Transcriptome In Vivo Analysis (TIVA)-Tag

Experiments were designed to develop a method for quantifying gene expression in individual identified live cells from the intact functioning tissue or organism. Without wishing to be bound by any particular theory, it is believed that development of such a method involves introducing a molecule into cells that when activated in a particular cell captures the RNA only in the cell that has been activated. That is, the activation of this molecule in intact tissue is spatially controlled.

The materials and methods employed in these experiments are now described.

Oligonucleotide Synthesis and Purification of the TIVA-Tag

Oligonucleotides were synthesized by standard phosphoramidite chemistry using an ABI DNA/RNA 394 nucleic acid synthesis system on a 1.0 mole scale.

Reagents were obtained from Glen Research including 2'Fluoro U (10-3430), 2'OMe A (10-3900), 5' thiol C6 (10-1936), Cy3 (10-5913), Cy5 (10-5915), and photocleavable spacer (10-4913) phosphoramidites, as was 3' biotin TEG CPG (20-2955). Coupling times were adjusted to manufacturer's recommendations, and 0.02 M iodine was used for oxidation steps.

After cleavage and deprotection using ammonium hydroxide at room temperature for 24 hours, oligonucleotides were purified on an Agilent 1100S reverse-phase HPLC (C18 column) with eluents of 0.05 M triethylammonium acetate (A) and acetonitrile (B); gradient, 0-40 min, 10-60% B, then 60-80% B in 40-50 min in A+B; flow rate, 1 mL/min. Removal of the 4,4'-dimethoxytrityl group was performed by treating the purified oligonucleotides with 80% acetic acid for 20 minutes at room temperature and drying under vacuum.

Some TIVA-tags contained both Cy3 and Cy5, while other variants contained either Cy3 or Cy5.

Figure 1:
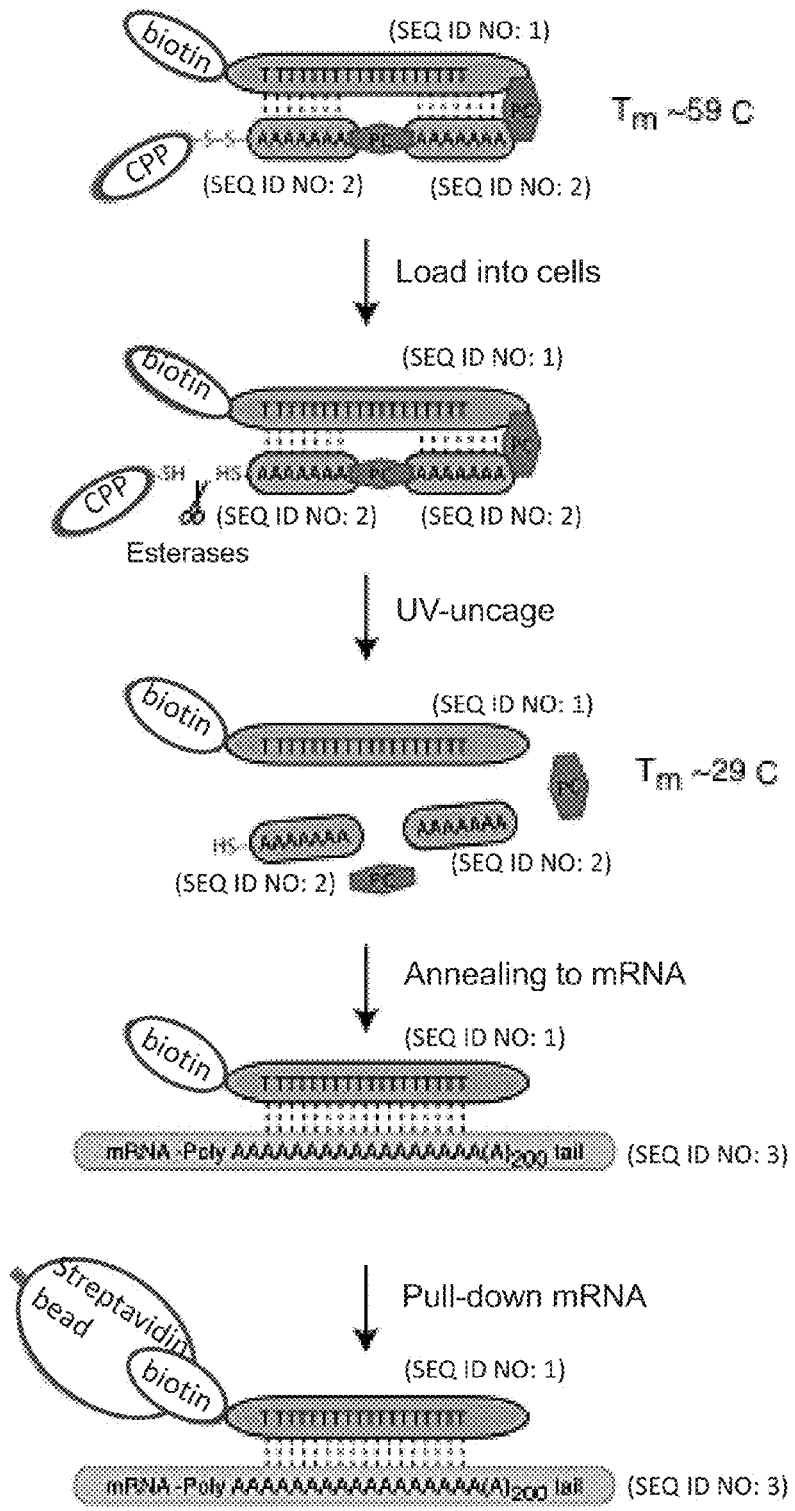
FIG. 1 is a schematic of the Transcriptome In Vivo Analysis (TIVA) procedure.
Figure 2:
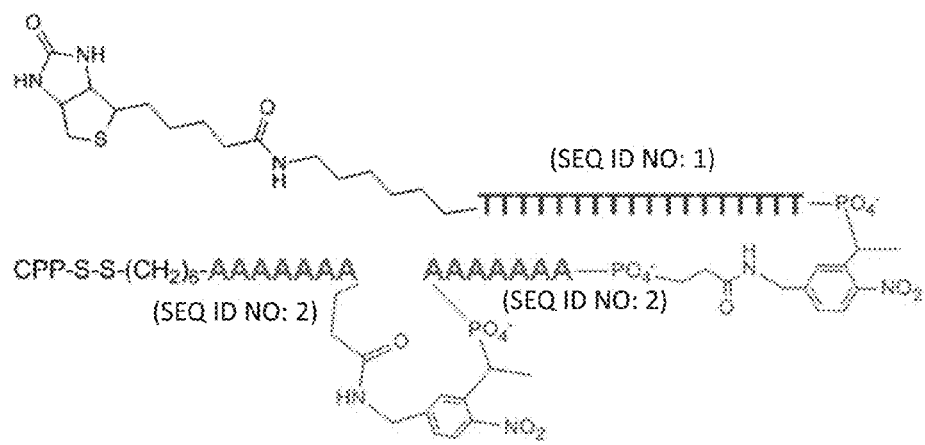
FIG. 2, comprising
Figure 2:
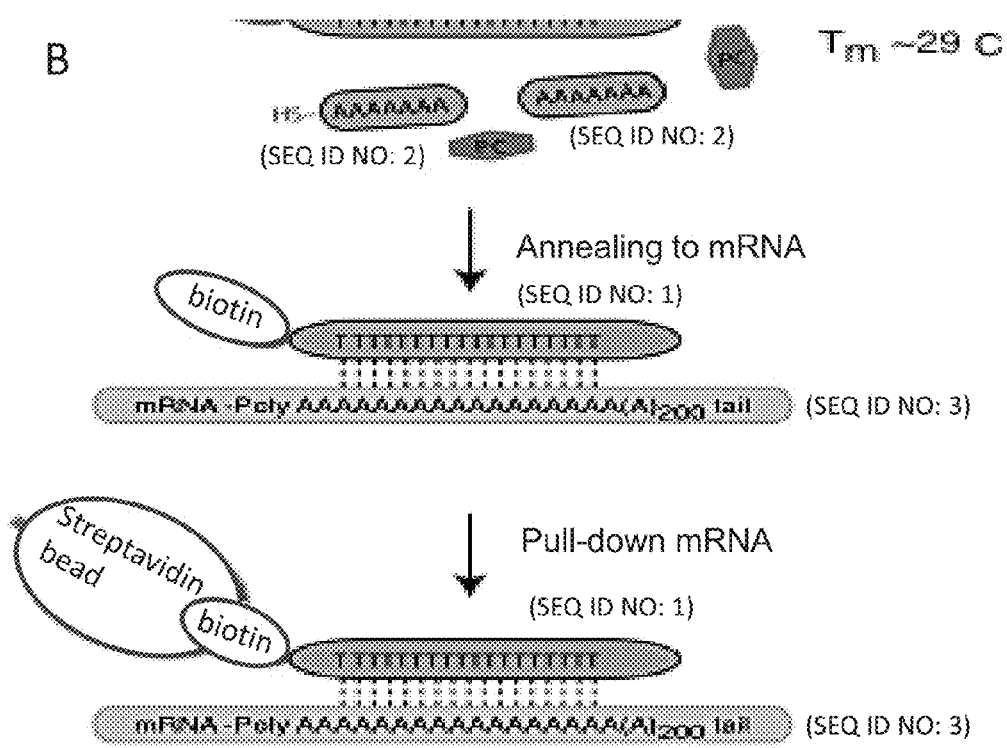
Figure 3:
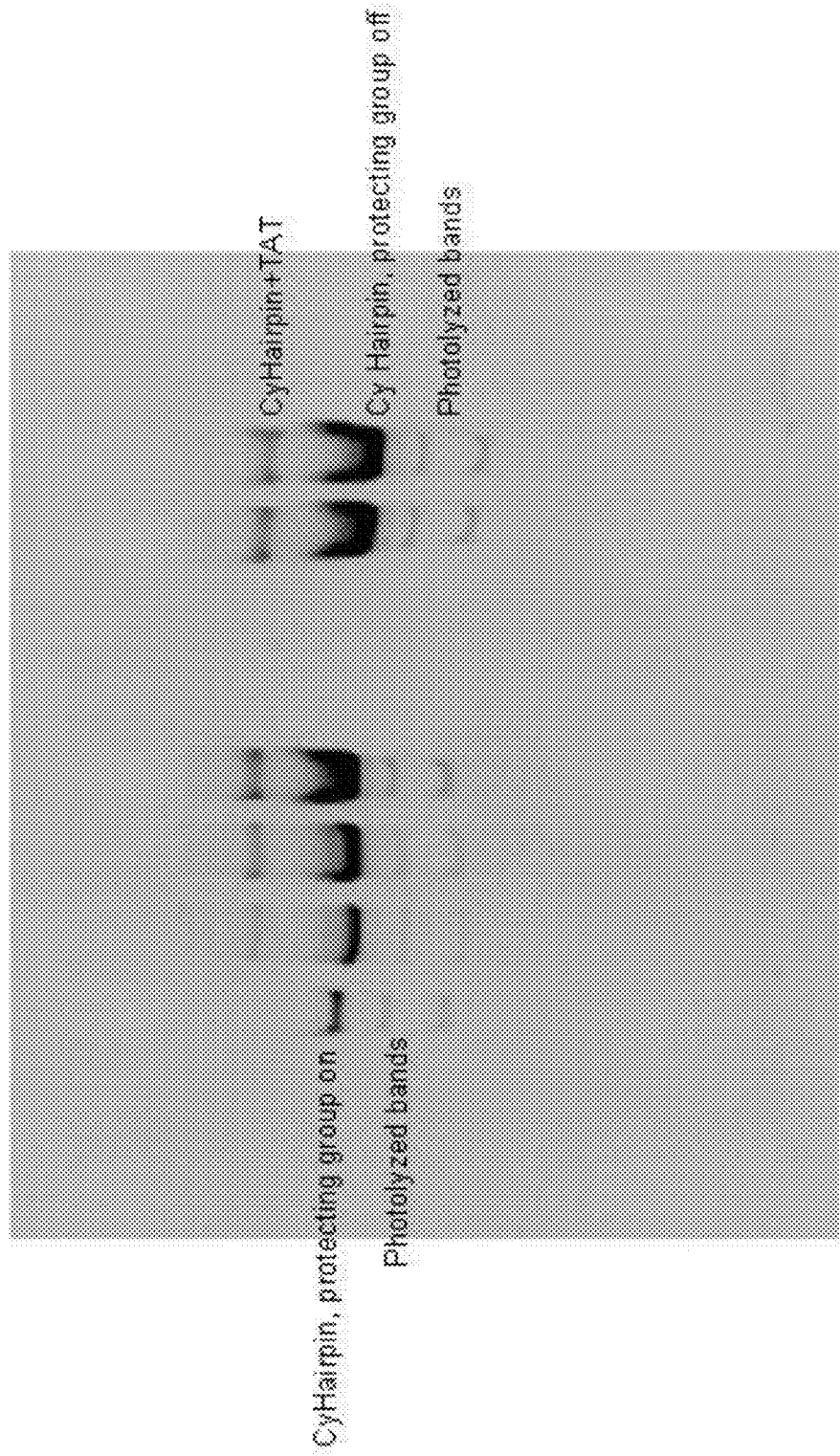
FIG. 3 is an image of a gel showing a representative TIVA-tag TAT peptide conjugation reaction. Lane 1 shows the unmodified Cy3/Cy5 labeled TIVA-tag before deprotection with TCEP. Lanes 2-6 show aliquots from the TAT-oligonucleotide conjugation reaction.

Conjugation of Oligonucleotides to Cell-Penetrating Peptides (FIG. 3)

The method of conjugating oligonucleotides to the CPPs through disulfide bonds was modified from Turner et al. (2005, *Nucleic Acids Research* 33: 27). Briefly, about 2 nmol of oligonucleotide with 5' thiol modification was deprotected using 50 mM TCEP for 2 hours. The TCEP was removed by desalting on a NAP-5 column (GE Healthcare) or HPLC, and the oligonucleotide was dried by lyophilization.

After drying, the oligonucleotide was redissolved in 30 µL of 0.33 M TEAA, 75 µL of formamide was added, and the sample was vortexed. The CPP in this case, TAT peptide with an activated Cys(Npys) residue, was obtained from Anaspec and dissolved at a concentration of 1 mM in water. To the dissolved oligonucleotide, 8 µL of the TAT solution was added, and the reaction was allowed to proceed overnight.

The reaction was then heated to 90° C. and loaded in 20 µL aliquots on a 20% polyacrylamide, 7M urea gel run at 300V for 60 minutes. The gel was visualized by UV shadowing on a TLC plate, and the bands representing the product were cut out. Alongside unmodified oligonucleotide, the TAT-conjugated product migrated slower and was easily separated. The bands from the gel were crushed with a pipet tip and soaked in TBE buffer overnight to recover the oligonucleotide-TAT product. It was then desalted on a NAP-10 column, concentrated, and characterized by MALDI at the Wistar Proteomics facility.

The modified method from Turner et al. was also followed to react the oligonucleotide with (D-Arg)$_9$ CPP. Approximately 4 nmol of oligonucleotide with 5' thiol modification was deprotected using 50 mM TCEP for 2 hours. The TCEP was removed by desalting on a NAP-5 column (GE Healthcare), and the oligonucleotide was dried by lyophilization. After drying, the oligonucleotide was redissolved in 50 µL of 0.33M TEAA, 150 µL of formamide was added, and the sample was vortexed. The (D-Arg)9 CPP with an activated Cys(Npys) residue from Anaspec was also dissolved at a concentration of 1 mM in water, and a 4-fold excess was added to the oligonucleotide. The reaction was allowed to proceed overnight and was purified by anion exchange HPLC using a 1 mL Resource Q column with a flow rate of 1 mL/min and a gradient of 0-100% buffer B in 30 min (buffer A: 20 mM Tris-HCl (pH 6.8), 50% formamide; buffer B: 20 mM Tris-HCl (pH 6.8), 50% formamide, 400 mM NaClO$_4$). Finally, the product was desalted on a NAP-5 column, concentrated, and characterized by MALDI as with the TAT-conjugated product.

Figure 4A:
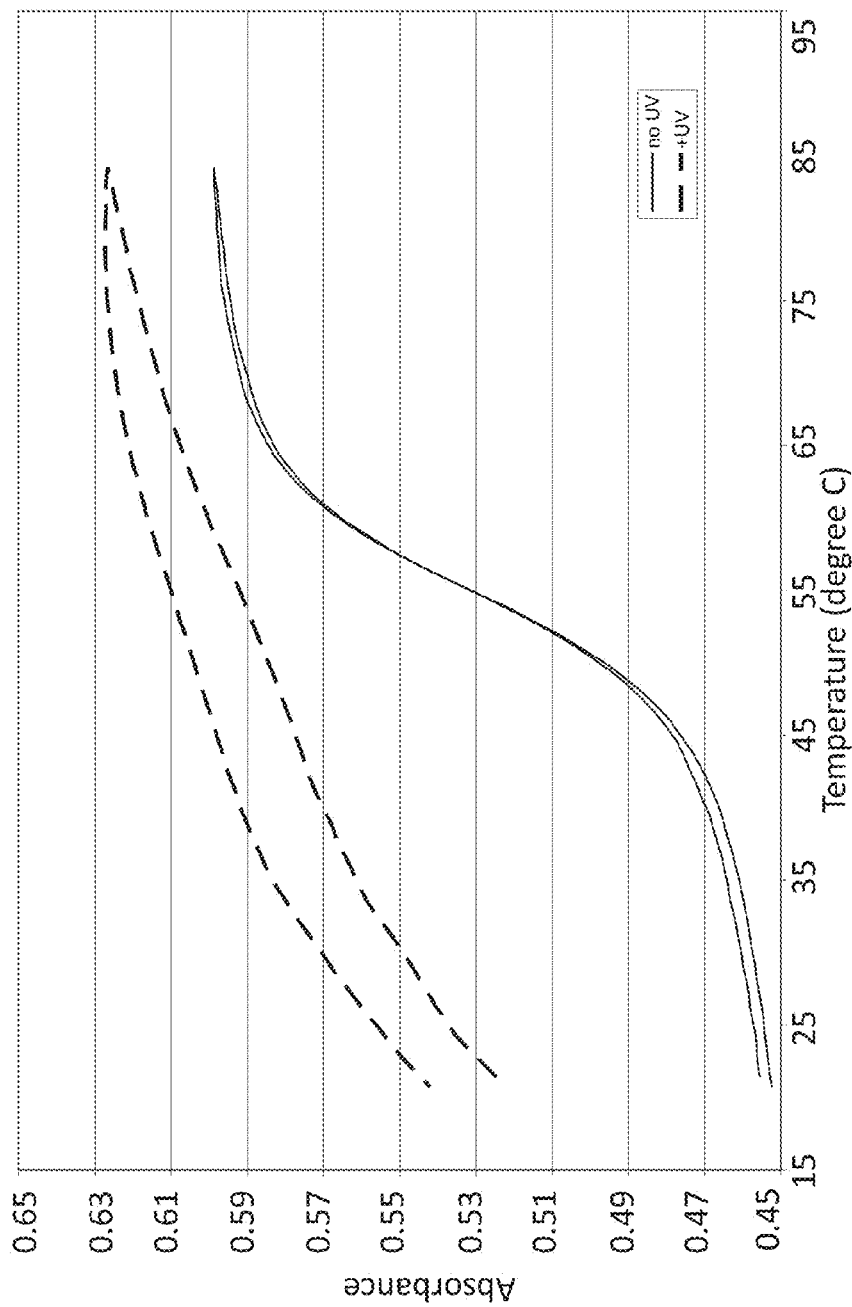
FIGS. 4A and 4B, is a series of images depicting melting point curves.
Figure 4B:
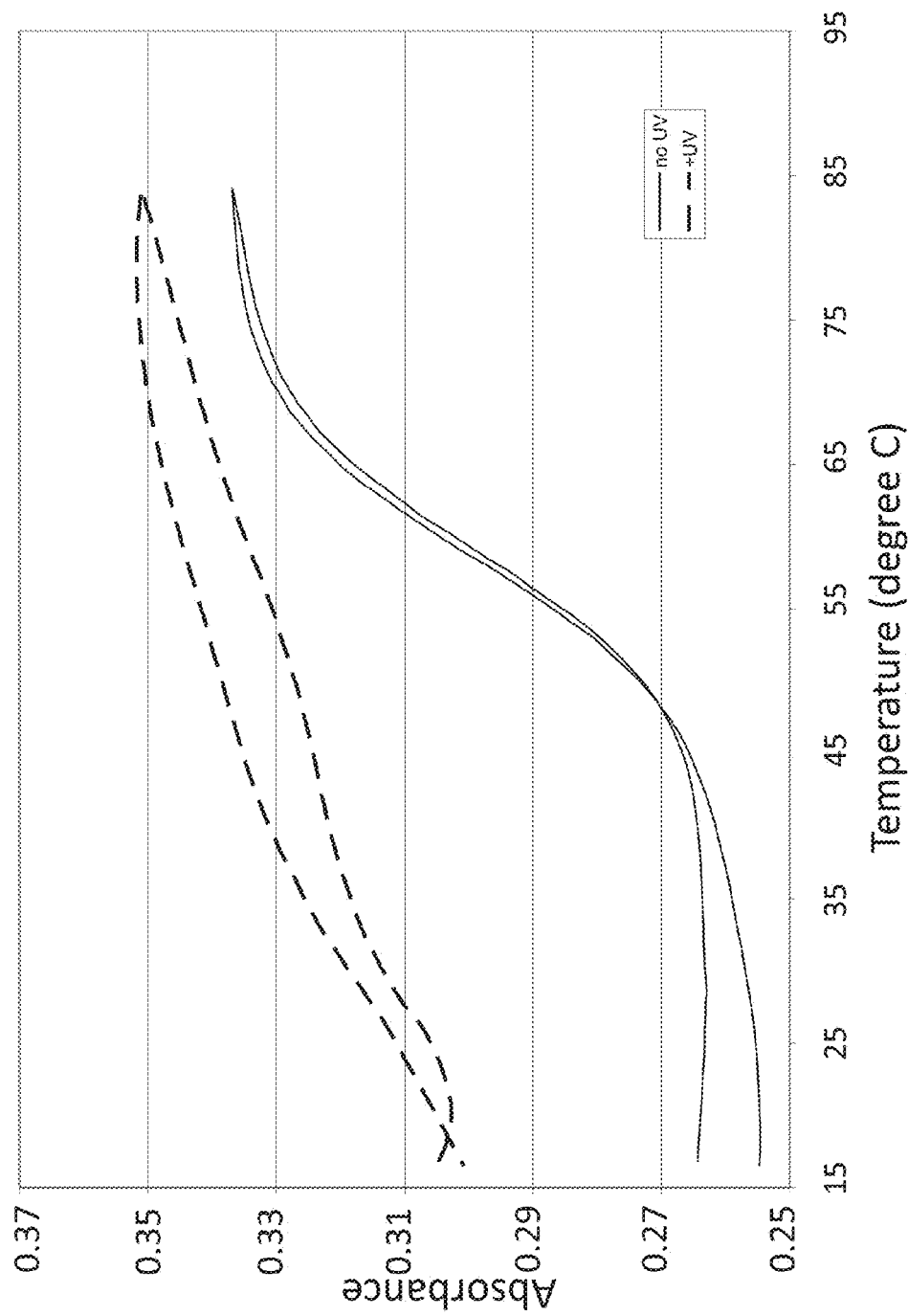

Melting Point Determination (FIG. 4)

Melting point studies were conducted on a Beckman Coulter DU800 UV-V is spectrophotometer equipped with a programmable Peltier temperature controller. Samples were monitored at 260 nm while heating or cooling at a rate of 1.0° C./min, with a 1-min hold per degree Celsius. Melting temperatures were determined from the peak of the first derivative plot of Abs$_{260}$ vs. temperature.

TIVA-tags were prepared at 1 M concentration in 10 mM Tris pH 7.5 with 300 mM NaCl and 10 mM MgCl$_2$. To make sure the TIVA-tags were properly annealed, the samples were heated to 90° C. for 5 minutes, then slowly cooled to room temperature over ~3 hours. For samples that were photolyzed, irradiation was carried out using an UV transilluminator (Spectronics Corporation TL-365R) at wavelengths centered on 365 nm (9 mW/cm$^2$ at peak intensity) with the sample in open 200 µL eppendorf tubes.

Figure 5:
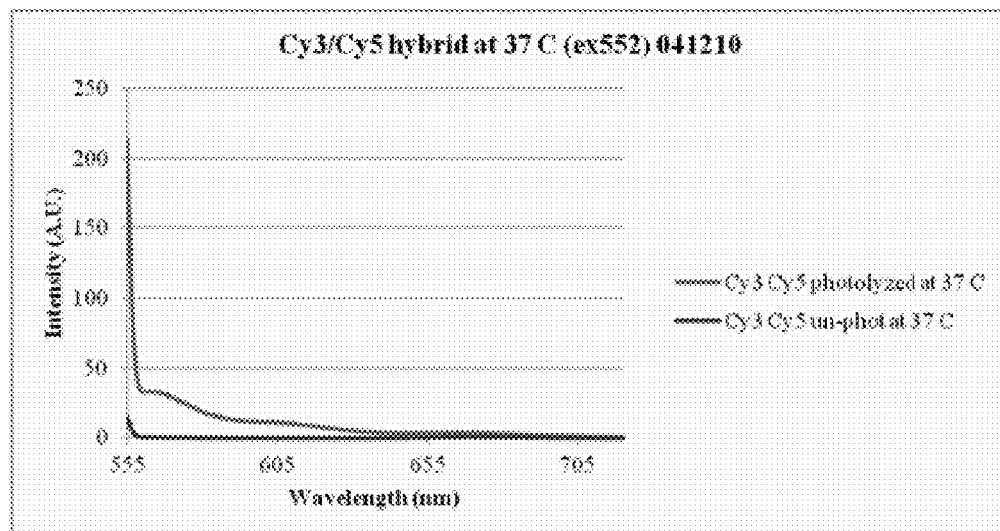
FIG. 5, comprising

FRET Analysis of Cy3/Cy5 Labeled TIVA-Tags (FIG. 5)

TIVA-tags with Cy3/Cy5 FRET fluorochrome pairs and TIVA-tags with only Cy5 fluorophore were prepared at 1 µM concentration in the same buffer as for the melting point determination experiments, and photolysis was carried out in the same way as above. The samples were incubated at 37° C. prior to measurement and then added to a sub-micro cuvette. The fluorescence emission of Cy3 at 565 nm and Cy5 at 667 nm, upon excitation at 552 nm, were monitored by a Varian Eclipse fluorimeter (scanning rate of 120 nm/min, and averaging time of 0.5000 s).

The FRET efficiency was defined as the intensity of the acceptor (Cy5) fluorescence divided by the intensity of the acceptor plus the donor (Cy3) fluorescence. In a preliminary experiment, the FRET efficiency was found to be 0.601 before photolysis, and 0.0996 afterwards. This is a change of 51% FRET efficiency. Additional fluorescence studies also performed with the Cy5-only TIVA-tag allowed for the Cy5 emission spectrum upon excitation at 552 nm to be subtracted from that of the Cy3/Cy5 TIVA-tag. This eliminated any contribution of Cy5 emission at 667 nm from the FRET measurements. Prior to photolysis, the FRET efficiency was 0.675, and it was 0.04621 post-photolysis. There is a 63% change in FRET efficiency, which signifies a conformational change in the TIVA-tag, i.e. a lysis of it into separate entities.

Figure 6:
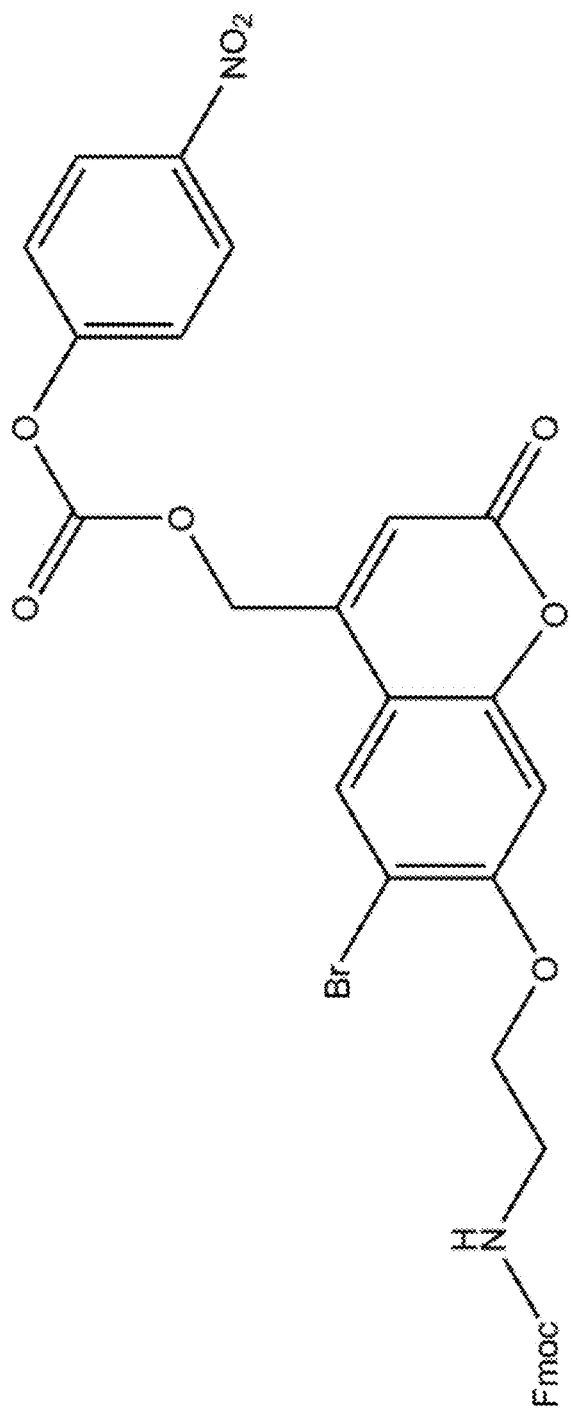
FIG. 6 is an image depicting the structure of bromocoumarin-based linker (2-photon cleavable) synthesized by Katayama et al. (2008, *Chemical Communications* 5399).

Synthesis of the Bhc-Coumarin Linker (FIG. 6)

The synthesis of the Bhc-coumarin linker was taken from Katayama et al. (2008 *Chemical Communications* 42: 5399-401).

Figure 7:
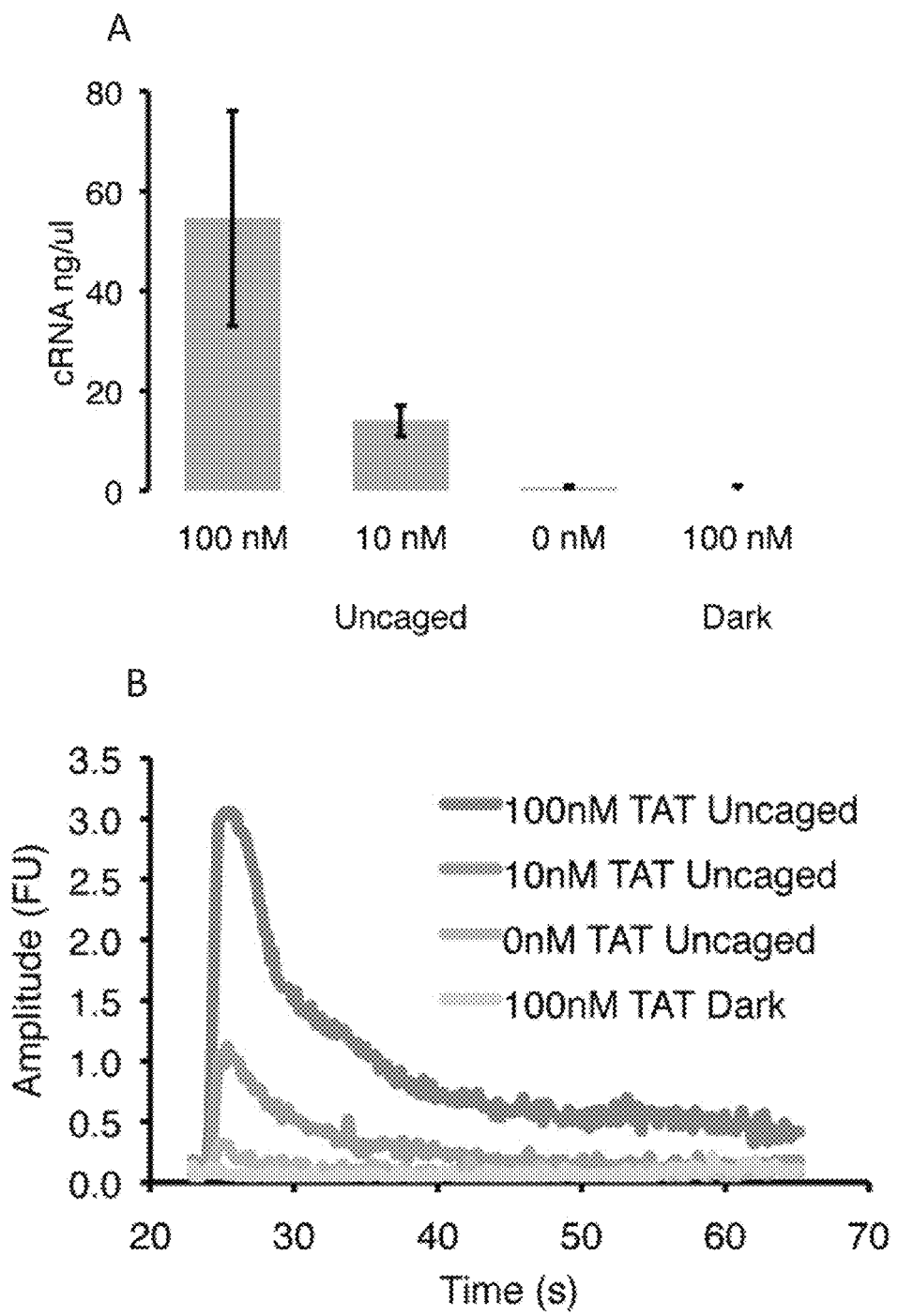
FIG. 7, comprising

Uncaging and mRNA affinity-purification using the TIVA-tag in live cells (FIG. 7 and To test the capacity of the TIVA-tag to uncage and bind mRNA in live cells, 8-10 days old hippocampal neurons on laminin-coated coverslips were used. Neurons were rinsed twice in pre-warmed and CO$_2$ calibrated MEM without phenol red, prior to incubation with the TIVA-tag (100 nM, 50 nM, 10 nM and 0 nM diluted in MEM without phenol red) at 37° C. and 5% CO$_2$ in the dark for 30 min. Coverslips were then rinsed three times in pre-warmed and CO$_2$ calibrated MEM without phenol red. Media was exchanged with 200 µl HBSS and neurons were uncaged under an inverted UV illuminator (312 nm) at ~7 cm distance and 5 min at room temperature. Control without uncaging, but with 100 nM TIVA-tag, was included. Following uncaging, the neurons were incubated in the dark for 30 min at room temperature. The media was then exchanged with 200 µl lysis buffer (20 mMTris-HCl pH 7.5, 600 mMNaCl, 20 mM MgCl2, 0.1% NP40, 1.85 U/µl RNasin and 5 mM DTT), and neurons were lysed under agitation at 4° C. for 20 min. The lysate was cleared and the supernatant was collected, and 10 µl magnetic streptavidin-T1-Dynabeads was added (beads were washed six times according to manufacturer's instructions followed by two washes in lysis buffer), and the suspension was incubated for 45 min on ice. The "unbound" fraction was collected on a magnet, and the Dynabeads were washed three times in 100 µl wash buffer (20 mM Tris-HCl, pH 7.5, 50 mM NaCl). To elute the bound mRNA on the Dynabeads, 9 µl ultrapure H$_2$O was added to the beads. The sample was then heated to 85° C. for 5 min and immediately after the supernatant was collected by separation on the magnet. The 9 µl of affinity-purified mRNA from one coverslip was T7-amplified two rounds according to the Eberwine protocol (see for example Van Gelder et al., 1990 Proc Natl Acad Sci USA 87: 1663-1667). The Bioanalyzer results for aRNA abundance and size distribution are shown in FIGS. 6 and 7, respectively. During a third round of T7 amplification, the samples were biotin labeled for Affymetrix microarray analysis.

In another set of affinity-purification experiments utilizing HEK 293T cells, the TIVA-tag (without CPP) was introduced into cells by lipofectamine transfection (Invitrogen). Briefly, HEK cells were rinsed and incubated in prewarmed Opti-MEM (Gibco) 1-2 hrs prior transfection. A lipofectamine:TIVA-tag mix was prepared by mixing 1 µl lipofectamine 2000 with 50 µl Opti-MEM, and 3 µl TIVA-tag with 50 µl Opti-MEM, respectively. Then, after 5 minutes the two mixtures were mixed and kept in the dark at room temperature for 15 min to allow complexes to form. After this incubation, 200 µl Opti-MEM was added, and the entire mixture was added to a 24-well with HEK cells. The cells were then kept in the dark and incubated for 1 hr at 37 C and 5% CO2. Then, excess TIVA-tag was washed away with Opti-MEM and the cells were uncaged under a 365 nm lamp for 30 seconds. A "dark" control was kept in the dark during this time. Both samples returned to the 37 C incubator for 15 minutes to allow the uncaged TIVA-tag to dissociated and bind mRNA. Then, the cells were lysed in 200 µl lysis buffer ((20 mMTris-HCl pH 7.5, 600 mMNaCl, 20 mM MgCl2, 0.1% NP40, 1.85 U/µl RNasin and 2 µg/ml poly A$_{20}$ oligo) at room temperature for 10 min. The lysate was collected and spun for 1 min at 13000 rpm. The supernatant was transferred to a new tube and 10 µl magnetic T1 Dynabeads (prewashed 5 times in wash buffer, and blocked for unspecific binding in 10 mM Tris-HCl pH 7.5, 300 mM NaCl, 10 mM MgCl2, and 5 mg/ml tRNA). After incubating for 15 min, the beads were collected on a magnet and washed five times in wash buffer. Then 9 µl H2O was added and the tube was incubated at 85 C for 1-2 min to elute the mRNA from the beads. The elate was separated from the beads using the magnet, and the 9 µl eluate was collected for further aRNA amplification as described above.

The results of the experiments are now described.

Transcriptome In Vivo Analysis (TIVA)

The results presented herein demonstrate the ability to introduce a molecule into cells that when activated in a particular cell captures the RNA only in the cell that has been activated. This method has been termed the Transcriptome In Vivo Analysis (TIVA) methodology. In this methodology, a hybrid nucleic acid molecule is synthesized, with functional groups that enable the molecule to go into any specific, selected or desired target cell, and when specifically activated within a single cell or subcellular compartment, the molecule anneals to the endogenous cellular RNA and permits its isolation (i.e., this molecule is called the TIVA-tag). Briefly, the structure of the molecule is composed of different functional groups: 1) A poly 2' fluoro-TTP (2FRNA). 18mer is synthesized that is connected to poly-A 14mer through a photocleavable linker. The poly-A is interrupted in the middle with a second photocleavable moiety. On the end of the 5' end of the poly 2' fluoro-TTP is a biotin molecule and in some iterations a fluorescent molecule. Upon uncaging of activation of the photocleavable moiety, the function of this group is to anneal and form a stable hybridization to endogenous RNA. 2) A cell penetrating peptide (CPP) is coupled to the 3' end of poly-A through a disulfide bond. The function of the CPP is to carry the molecule into cells. Once inside cells, the CPP is removed from the molecule by reduction of the disulfide bond catalyzed by endogenous enzymes. This nucleic acid component of the TIVA-tag remains inactive at physiological temperatures and does not bind to cellular poly-A RNA unless the molecule's endogenous poly 2' fluoro-TTP::polyA self-annealing is eliminated. 3) The function of the two photocleavable linkers is to activate the RNA binding ability of the molecule by photouncaging. UV light covalently cleaves the photocleavable linker. The annealed poly 2' fluoro-TTP and poly-A is destabilized by the cleavage of the photocleavable linkers, which when cleaved gives rise to two 7-mer poly-As that do not form a stable hybrid with the poly 2' fluoro-TTP, and diffuses away leaving the poly 2' fluoro-TTP as a free entity that can then anneal to the long poly-A tail of an endogenous cellular mRNA. 4) A biotin molecule is covalently attached to the poly 2' fluoro-TTP, facilitating the isolation of poly 2'fluoro-TTP:cellular RNA hybrids. The poly 2' fluoro-TTP:cellular RNA hybrids are isolated using either beads conjugated with streptavidin or antibodies to biotin. Upon isolation, the RNA can then be analyzed using standard procedures including a RNA T7 amplification, PCR, microarray or NextGen sequencing.

The activation of the compounds that have been tested occurs through UV-induced cleavage of the photocleavable compound. The next generation compound can have 2-photon-cleavable moieties where the photocleavable linkers are currently positioned. The 2-photon groups permit uncaging in selected cells in individual cells in culture, cells in the live slice and cells in the intact animal. This strategy permits isolation of the RNA from a single cell in a population of interconnected cells. Also, this strategy can also permit isolation of RNA from cellular subregions such as dendrites or axons that are in contact with other cells. The results presented herein demonstrate that the strategies discussed herein can also be of great utility in looking at individual neoplastic cells in a tissue or tumor.

A number of current techniques have attempted to generate whole genome expression profiles from cells in situ (Table 1). However, all these techniques select a given cell or population of cells based on the expression of a particular marker. An emerging consensus acknowledges that no marker truly identifies a single cell type, thus calling for a method combining marker identification with real-time physiological techniques. The TIVA techniques discussed herein can select single cells, subcellular regions of cells or populations of cells based on marker expression, anatomical location, as well as physiological and electrophysiological in vivo techniques. Therefore, the TIVA techniques of the invention are a breakthrough for the understanding of gene expression in intact tissues.

TABLE 1 mRNA collection methods for intact tissue preparations

| mRNA Collection Method | Cell Selection Parameters | | | | |
|---|---|---|---|---|---|
| | Molecular marker | Cell morphology | Subregional location | Single cell physiology | Subcellular resolution |
| TIVA-tag | + | + | + | + | + |
| FACS | + | − | − | − | − |
| LCM | + | + | + | − | − |
| TRAP | + | − | − | − | − |

Example 2

Caged TIVA-Tags

Messenger RNAs in a cell have polyadenine tails that aid in translation, thus an antisense oligonucleotide consisting of all uracils can hybridize to this region. An RNA analog with increased thermal stability, 2'-fluoro RNA, was used to target cellular RNA. The fluoro group at the 2' position locks the ribose ring into the 3' endo conformation, causing duplexes of the modified RNA to favor A-form helices and increasing melting temperature by 2° C. per base relative to DNA (Kawasaki et al., 1993 Journal of Medicinal Chemistry 36: 831). One advantage of using 2'-fluoro RNA is that the caged version can be synthesized as a single molecule in one day with a DNA synthesizer using a photocleavable spacer.

In addition to the 2'-fluoro RNA antisense strand, design of the caged molecule includes the photocleavable spacer joined to the blocking strand, a 3' biotin tag, and a 5' thiol. The blocking strand consists of 2'-OMe RNA, which also increases thermal stability and nuclease resistance of the duplex. The 3' biotin tag allows the antisense strand bound to cellular mRNA to be isolated easily using magnetic streptavidin beads, after transfection and lysis of the cells. The 5' thiol is installed to allow conjugation of the molecule to a cell-penetrating peptide (CPP). A FRET pair was also designed to be incorporated at the 3' end of the antisense strand and the 5' end of the blocking strand. This allows monitoring the dissociation of the two strands upon photolysis. The standard Cy3/Cy5 fluorophores were chosen because they do not absorb at wavelengths below 400 nm.

In summary, the 2'-fluoro RNA is designed to bind the polyA tails of all mRNAs in a photolyzed cell and, after lysis, the hybridized 2'-fluoro RNA/mRNA can be affinity-purified by magnetic streptavidin beads. Heating recovers the mRNA and the transcript is amplified to determine what is present in the cell. Caging the 2'-fluoro oligonucleotide allows uncaging in single cells, and the RNA population from single cells to be identified (FIG. 8).

In affinity-purification assays, 18-mer 2'-fluoro RNA consisting of all uracils and a biotin tag was shown to isolate RNA in vitro. Melting temperatures were measured for this biotin-tagged 18-mer and complementary 2'-OMe RNAs of lengths 5, 7, 9, 11, 13, and 15 nucleotides (Table 2). Oligonucleotides were prepared at 1 µM concentration in 10 mM Tris pH 7.5 with 300 mM NaCl and 10 mM $MgCl_2$, the same buffer used in all affinity-purification assays and cell experiments. To ensure the oligonucleotides were properly annealed, the samples were heated to 90° C. for a few minutes, and then incubated at 37° C. for at least 1 h. Melting studies were conducted on a Beckman Coulter DU800 UV-Vis spectrophotometer equipped with a programmable Peltier temperature controller. Samples were monitored at 260 nm while heating or cooling at a rate of 1.0° C./min, with a 1-min hold per degree Celsius. Melting temperatures were determined from the peak of the first derivative plot of $Abs_{260}$ vs. temperature.

TABLE 2

Melting temperatures of 2'-OMe RNA oligonucleotides consisting of all adenines against a 18-mer 2'-fluoro RNA consisting of all uracils at 1 μM concentration in 10 mM Tris pH 7.5 buffer with 300 mM NaCl and 10 mM $MgCl_2$.

| Length | Melting Temperature (° C.) |
|---|---|
| 5 | 18 |
| 7 | 24 |
| 9 | 31 |
| 11 | 39 |
| 13 | 45 |
| 15 | 50 |

Figure 9A:
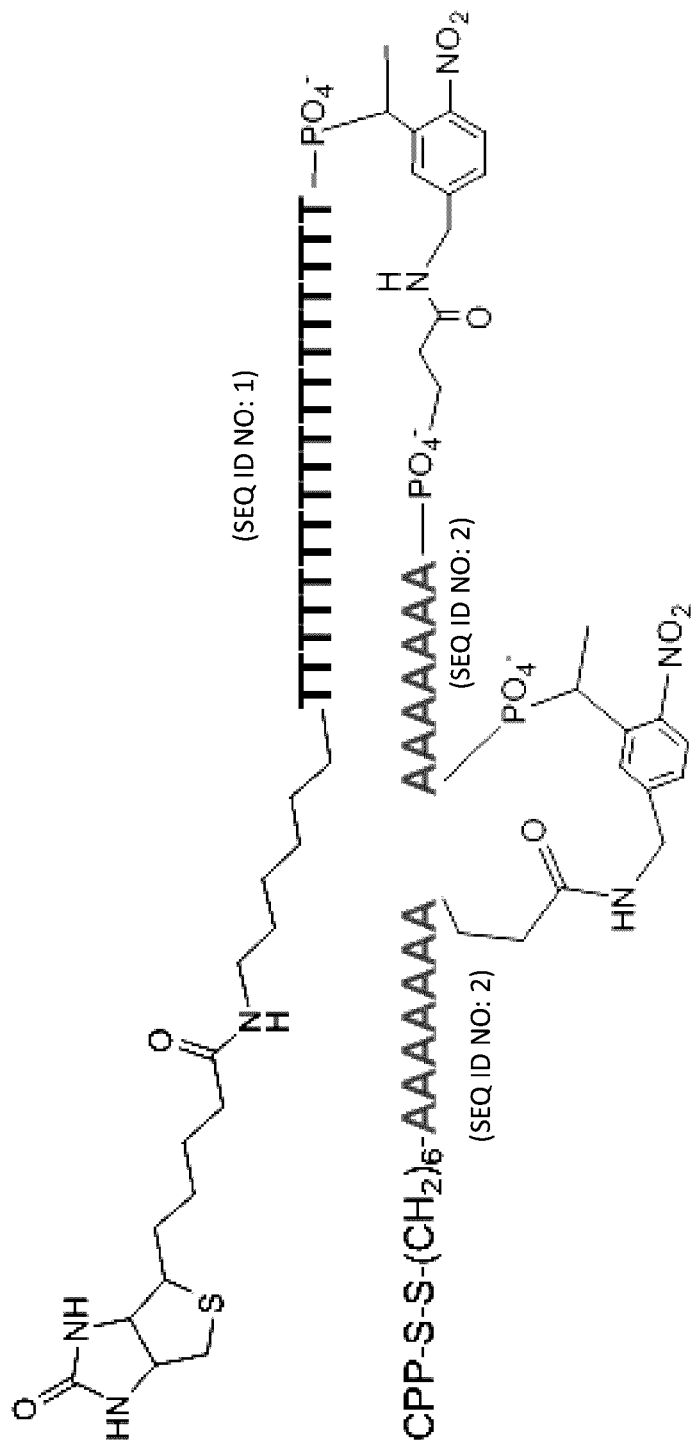
FIGS. 9A and 9B, is a series of images depicting structures of 2'-fluoro RNA TIVA-tag with (FIG. 9B) and without (FIG. 9A) Cy3/Cy5 dyes.
Figure 9B:
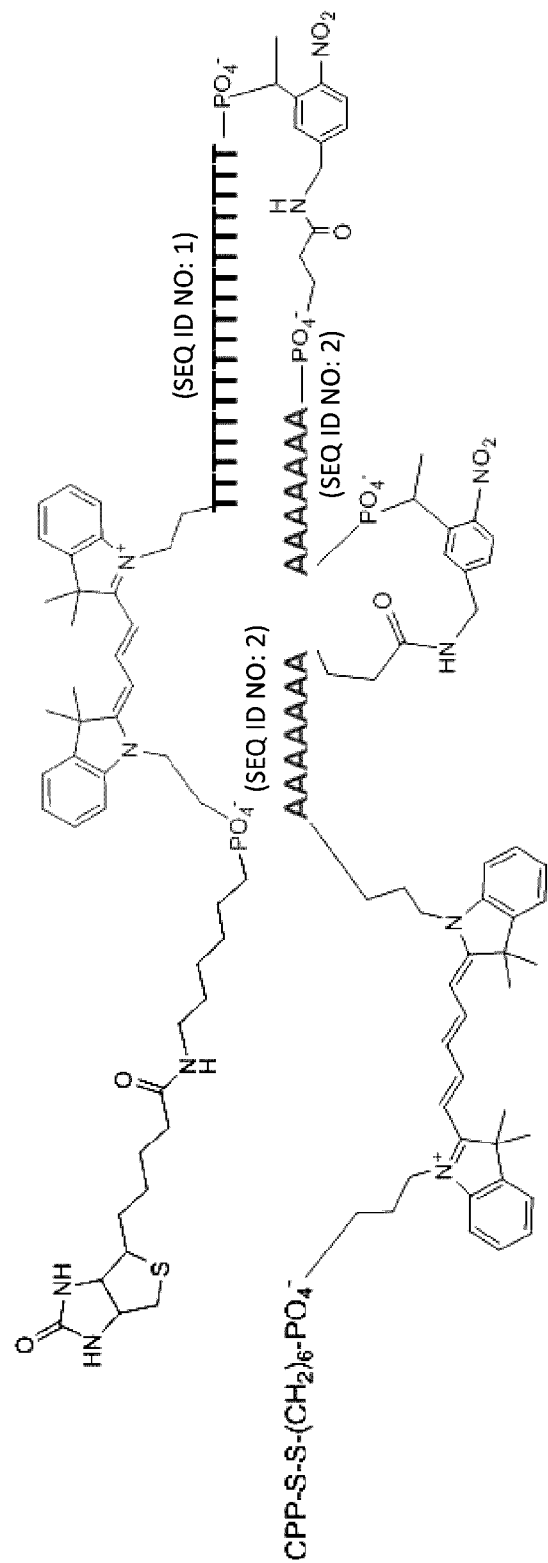

A 7-mer 2'-OMe RNA had a melting temperature of around 24° C., much lower than the temperature used for cell experiments, 37° C., so the TIVA-tag was designed to be an 18-mer 2'-fluoro oligonucleotide connected to two 7-mer 2'-OMe oligonucleotides using two photocleavable spacers without fluorophores (FIG. 9A) and with the Cy3/Cy5 FRET pair (FIG. 9E).

The caged TIVA-tags were synthesized as a single strand by standard phosphoramidite chemistry using an ABI DNA/RNA 394 nucleic acid synthesis system on a 1.0 mole scale. Reagents were obtained from Glen Research including 2'-fluoro U, 2'-OMe A, 5' thiol C6, Cy3, Cy5, and photocleavable spacer phosphoramidites, as was 3' biotin TEG CPG. Coupling times were 6 min for the 2'-OMe phosphoramidites and 3 min for all others, and 0.02 M iodine was used for oxidation steps.

After cleavage and deprotection using ammonium hydroxide at room temperature for no more than 24 h, oligonucleotides were purified on an Agilent 1100S reverse-phase HPLC (C18 column) with eluents of 0.05 M triethylammonium acetate (A) and acetonitrile (B); gradient, 0-40 min, 10-60% B in A+B; flow rate, 1 mL/min. Removal of the 4,4'-dimethoxytrityl group was performed by treating the purified oligonucleotides with 80% acetic acid for 20 min at room temperature and drying under vacuum.

The next set of experiments was designed to assess the melting temperature of each TIVA-tag under the same conditions used above. For the photolyzed sample, irradiation was carried out using an UV transilluminator (Spectronics Corporation TL-365R) at wavelengths centered on 365 nm (9 mW/$cm^2$ at peak intensity) with the sample in open 200 μL Eppendorf tubes.

Figure 10A:
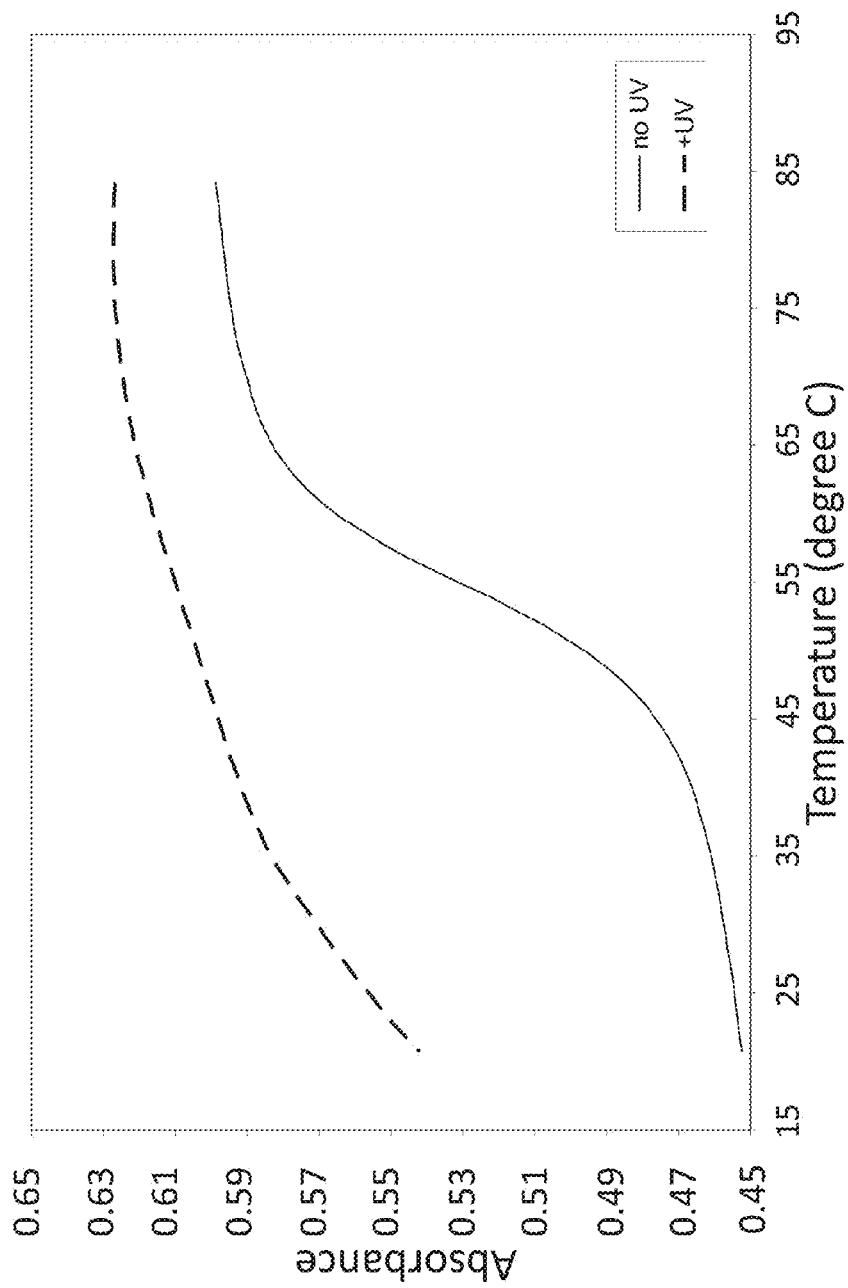

Before photolysis the melting temperature of the non-fluorescently-labeled TIVA-tag was 56° C., and after photolysis, it dropped to 32° C. (FIG. 10A). The Cy3/Cy5-labeled TIVA-tag had similar melting temperatures of 59° C. before photolysis and 29° C. afterwards (FIG. 10B). This modulation ($\Delta T_m \approx 30°$ C.) was promising, so the TIVA-tags were then tested for their ability to affinity-purify RNA in vitro. The photolyzed TIVA-tags were able to affinity-purify RNA, while the intact TIVA-tags affinity-purified. With these results, the TIVA-tags were then tested in cell culture.

To transport the TIVA-tag into cells, it was conjugated to a cell-penetrating peptide through a disulfide linkage. The disulfide bond is reduced after entering the cell and thus dissociates from the TIVA-tag. The method of conjugating oligonucleotides to the cell-penetrating peptide through disulfide bonds was modified from Turner (2005 *Nucleic Acids Research* 33: 27). Briefly, about 2 nmoles of oligonucleotide with 5' thiol modification was deprotected using 50 mM TCEP for 2 h. The TCEP was removed by desalting on a NAP-5 column (GE Healthcare) or HPLC, and the oligonucleotide was dried by lyophilization. After drying, the oligonucleotide was redissolved in 30 μL of 0.33 M TEAA, 75 μL of formamide was added, and the sample was vortexed. TAT peptide with cysteine activated with a 3-nitro-2-pyridinesulfenyl group (Npys) on the C-terminus, C(Npys)YGRKKRRQRRR—$NH_2$, was obtained from Anaspec and dissolved at 0.1 mM concentration. To the dissolved oligonucleotide, about a four-fold molar excess of the TAT solution (8 nmoles) was added, and the reaction was allowed to proceed overnight.

The reaction was then heated to 90° C. degrees and loaded in 20 μL aliquots on a 20% polyacrylamide, 7 M urea gel run at 300 V for 60 min. The gel was visualized by UV shadowing on a TLC plate and the bands representing the product were cut out. Alongside unmodified oligonucleotide, the TAT-conjugated product migrated slower and was easily separated (FIG. 3). The bands from the gel were crushed with a pipet tip and soaked in TBE buffer overnight to recover the oligonucleotide-TAT product. It was then desalted on a NAP-10 column and concentrated.

The non-fluorescent TIVA-tag has already been tested in rat hippocampal neuron cultures. At 7-12 days old, the cells were incubated with 100 nM TAT-TIVA-tag for 30 min at 37° C. and uncaged for 5 min under inverted illuminator at 312 nm. After 30 min at room temperature, the cells were lysed and magnetic streptavidin beads were used to isolate the antisense strand bound to mRNA. The mRNA was eluted by heating to 85° C. and amplified by the Eberwine inverse transcription method (Phillips et al., 1996 *METHODS: A Companion to Methods in Enzymology*, Vol. 10, pp. 283). After photolysis, the uncaged TIVA-tag was able to recover 10-20% of the total cellular RNA after photolysis with no RNA recovered before photolysis.

Figure 11A:
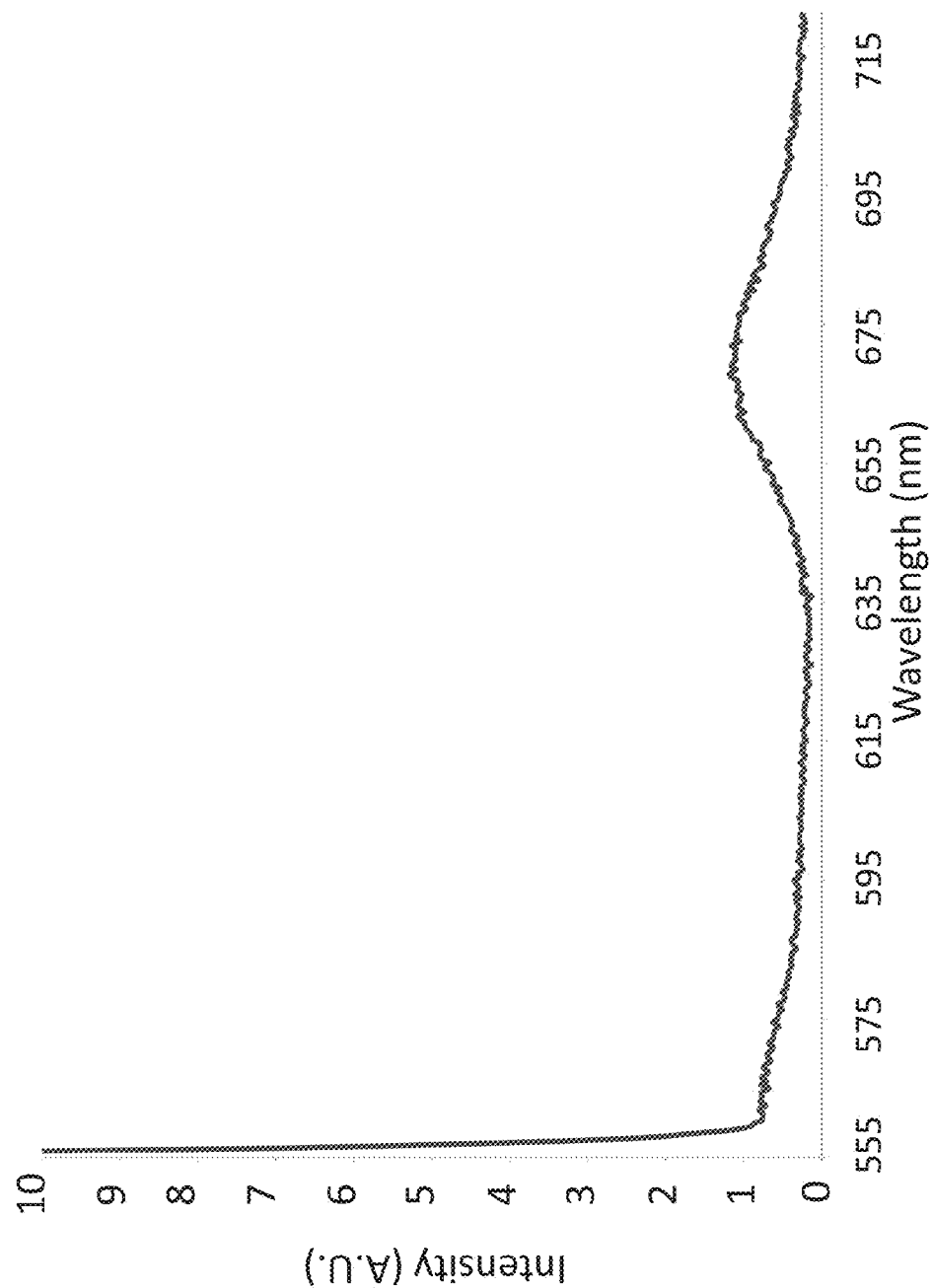
FIGS. 11A and 11B, depicts a wavelength scan of Cy3/Cy5 labeled TIVA-tag excited at 552 nm, before (A) and after photolysis (B).
Figure 11B:
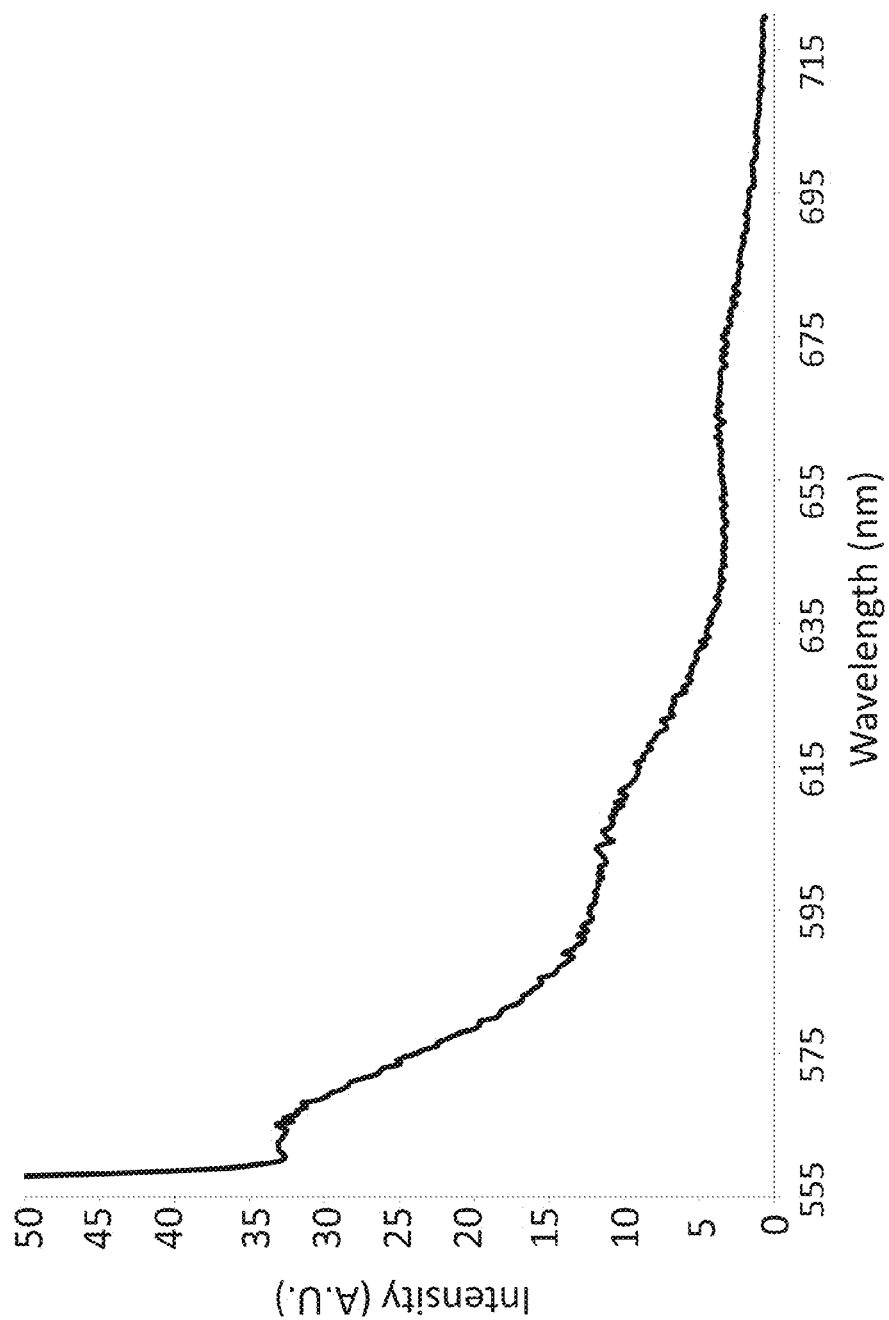
Figure 12:
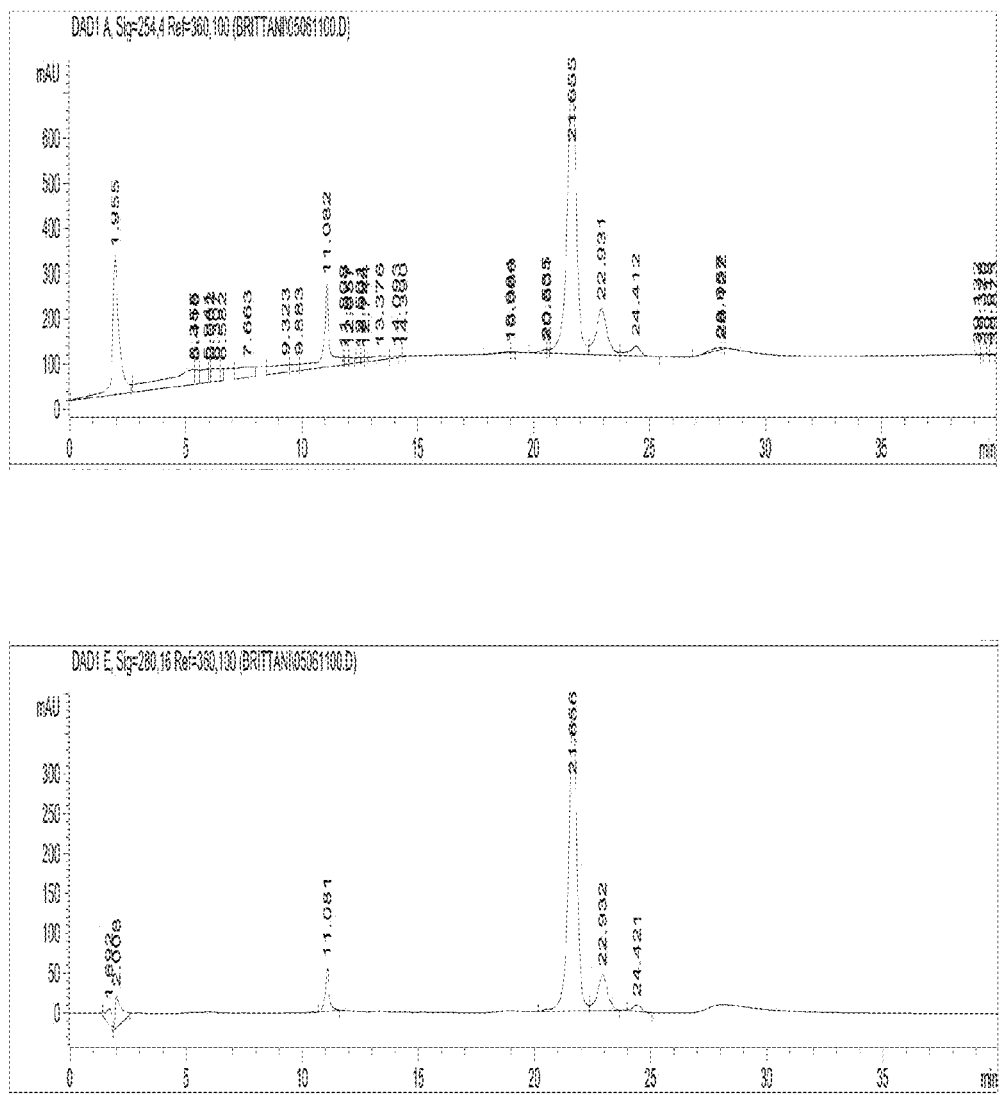
FIG. 12 depicts HPLC chromatograms showing purification of (D-Arg)-9-Cy-TIVA. The 21.6 min peak is CPP-conjugated product, the mass of which was determined by MALDI mass spectrometry (see FIG. 13). The trace at 254 nm monitors the oligonucleotide.
Figure 13:
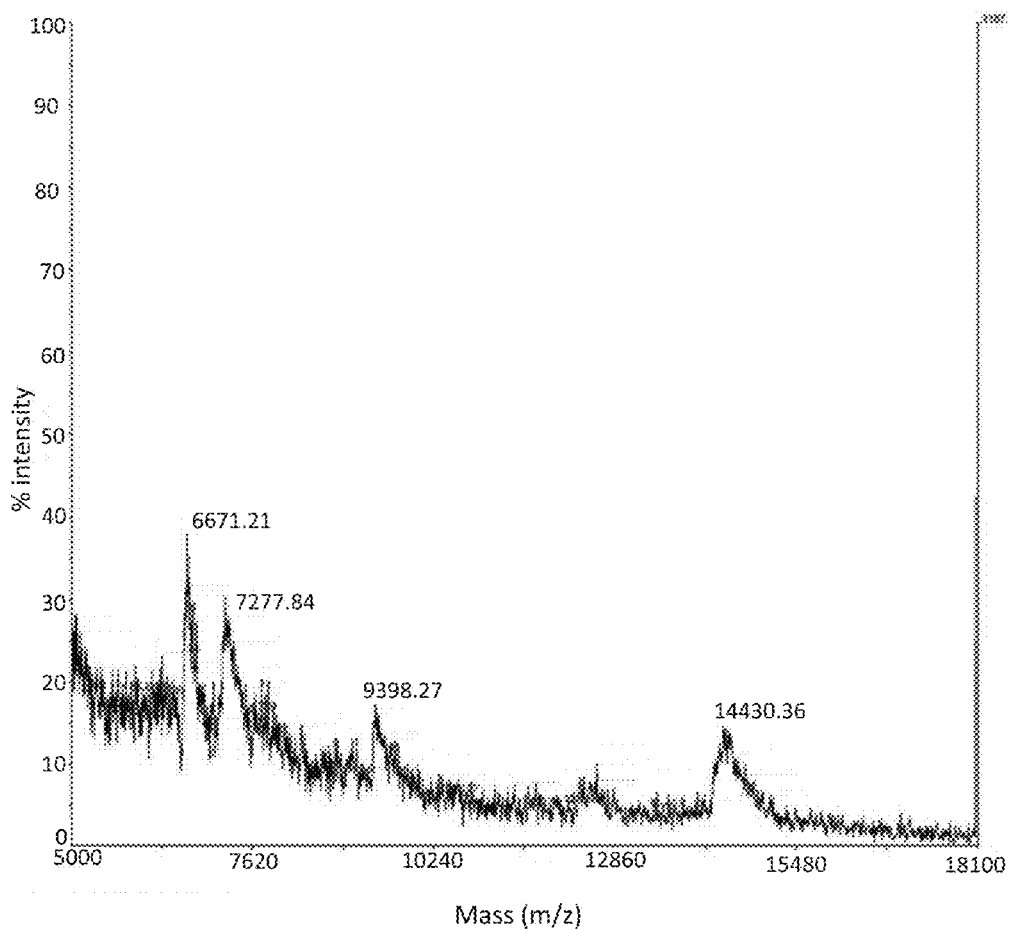
FIG. 13 depicts the results of a study using MALDI MS in negative ion mode with 3-hydroxypicolinic acid (HPA) (expected mass: 14,413; MALDI mass: 14,430; peaks at 9398, 7277, 6671 correspond to photolyzed fragments).

The next set of experiments was performed to measure the FRET efficiency of the dual labeled Cy3/Cy5 TIVA-tag before and after photolysis. The samples were prepared at the same concentrations in the same buffer as for the melting temperature experiments. The fluorescence emission of Cy3 at 565 nm and Cy5 at 667 nm, upon excitation at 552 nm, was monitored by a Varian Eclipse fluorimeter (scanning rate of 120 nm/min. and averaging time of 0.5000 s). The FRET efficiency was defined as the intensity of the acceptor (Cy5) fluorescence divided by the total fluorescence intensity of the acceptor (Cy5) plus the donor (Cy3). Prior to photolysis, the FRET efficiency was 0.60 (FIG. 11A), and afterwards, 0.10 (FIG. 11B). This 6-fold decrease in FRET efficiency upon photolysis strongly suggests dissociation of the oligonucleotides.

The goal of using a hybrid of a photoactivatable linker and oligos was to create a longer blocking strand that would still have a low melting temperature upon photolysis. The results presented herein demonstrate that the resulting TIVA-tag is very stable in the cellular environment, as predicted by in vitro melting temperature measurements. For optimizing transfection into a cell, synthesizing a conjugate using the Transportan CPP or the TAT CPP may improve delivery. The results presented herein are the first example of using fluorophore reporters to monitor the dissociation of a caged TIVA-tag.

Example 3

Folate-TIVA-Tag

Figure 14:
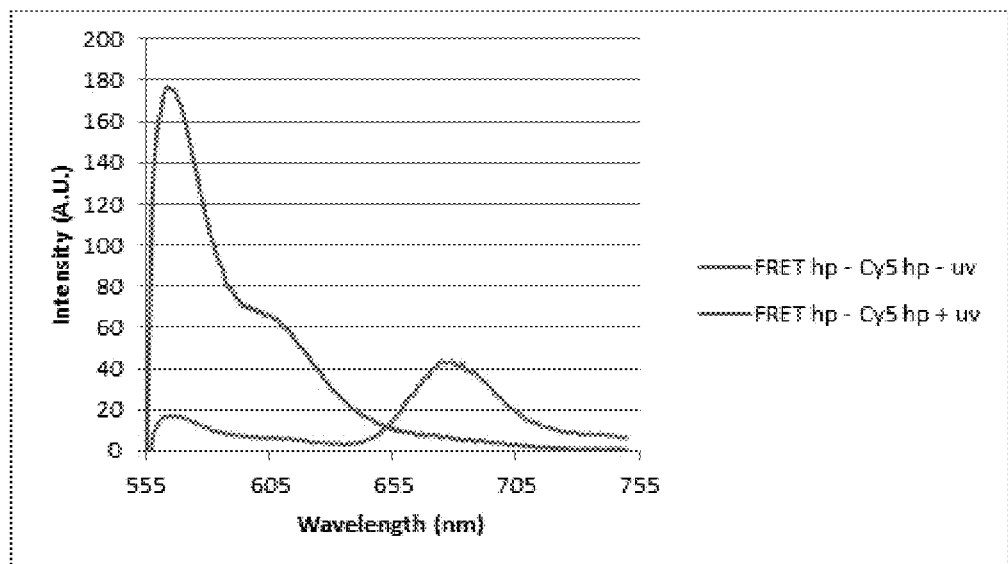
FIG. 14 depicts the results of a study performing a wavelength scan of Cy3/Cy5 labeled TIVA after subtraction of Cy5-only TIVA emission spectrum. Results before and after photolysis are shown. Also shown are intensities at different wavelengths and the ratio of acceptor Cy5 intensity divided by the total intensity of Cy3 and Cy5 emission.
Figure 15:
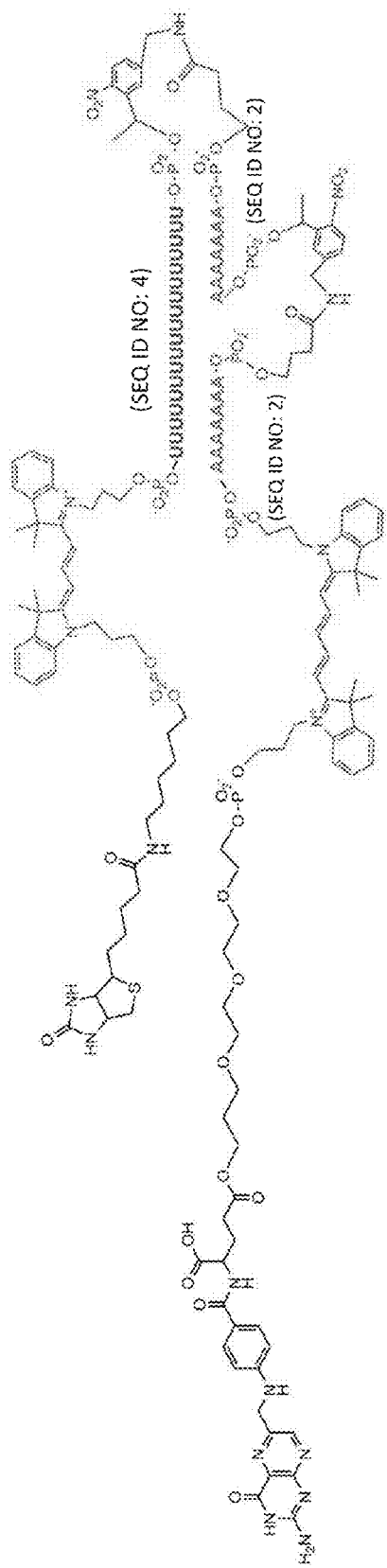
FIG. 15 is an image depicting an exemplary structure of a folate TIVA-tag.

TIVA constructs were designed and developed to include folate as the CPD (FIG. 14). Attachment of folate to the TIVA construct targets entry of the construct into a cell through folate receptor mediated endocytosis. This construct thereby targets entry into cells that express folate receptor on the cell surface. The folate-TIVA construct will therefore be useful in profiling the RNA in cancer, as some cancer cells express large numbers of folate receptors.

Oligonucleotides were synthesized by standard phosphoramidite chemistry using an ABI DNA/RNA 394 nucleic acid synthesis system on a 1.0 mole scale. Reagents were obtained from Glen Research including 2' Fluoro U (10-3430), 2' OMe A (10-3100), 5' thiol C6 spacer (10-1936), Cy3 (10-5913), Cy5 (10-5915), and photocleavable spacer (10-4913) phosphoramidites, as was 3' biotin TEG CPG (20-2955). For the Folate TIVA-tag, a 5'-Folate-TEG phosphoramidite was attained from Berry and Associates (BA 0349) and incorporated at the 5' end of the molecule instead of the thiol C6 spacer. Coupling times were adjusted to manufacturer's recommendations, and 0.02 M iodine was used for oxidation steps.

After cleavage and deprotection using ammonium hydroxide at room temperature for 24 hours, oligonucleotides were purified on an Agilent 1100S reverse-phase HPLC (C18 column) with eluents of 0.05 M triethylammonium acetate (A) and acetonitrile (B); gradient, 0-40 min, 10-60% B, then 60-80% B in 40-50 min in A+B; flow rate, 1 mL/min; 40° C. The retention time of the purified TIVA-tags with 5' thiol modification was ~50 min. HPLC purification of the Folate TIVA-tag required a gradient of 10-60% B in 60 min at 40° C. with a flow rate of 1 ml/min. The retention time for the Folate TIVA-tag was ~26 min. Removal of the 4,4'-dimethoxytrityl group was performed by treating the purified oligonucleotides with 80% acetic acid for 20 minutes at room temperature. The TIVA-tag was desalted on a Nap-5 column (GE) and dried under vacuum.

Figure 16:
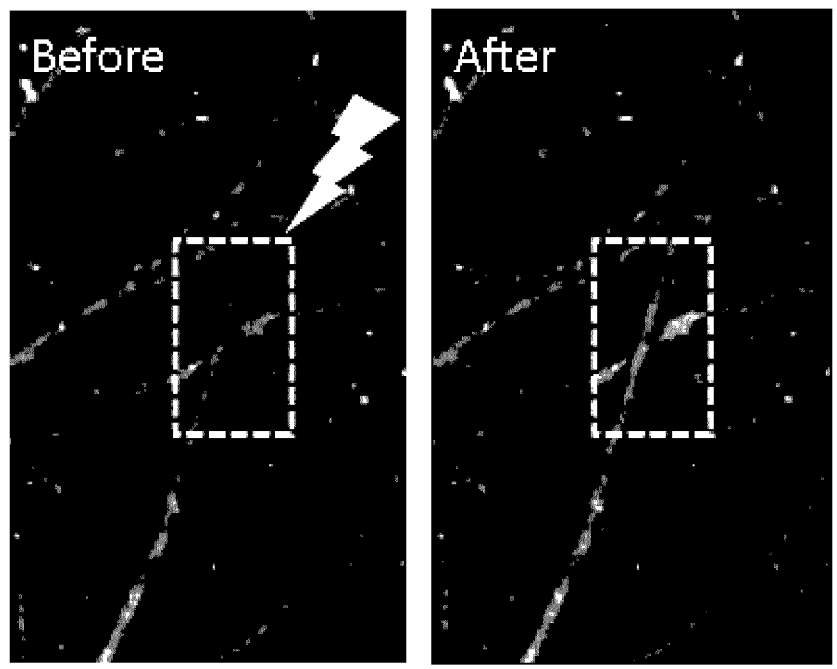
FIG. 16 is a set of images demonstrating the successful activation of folate TIVA-tag in a dendrite of a neuron. Uncaged folate-TIVA-tag is visualized based on the change in FRET signal following irradiation of the target area by the laser.

Neurons were loaded with Folate-TIVA-tag. A laser was focused onto a specific target area, which included the presence of several dendrites. Irradiation of the target area uncaged the Folate-TIVA-tag. Uncaging of the Folate-TIVA-tag was visualized based on the change in FRET signal from a dominant Cy5 signal to a dominant Cy3 signal (FIG. 16).

The data presented herein demonstrate that Folate-TIVA-tag has the ability to enter cells and be uncaged when irradiated.

Example 4

TIVA-Tag Activation in Slice Preparation

Figure 17:
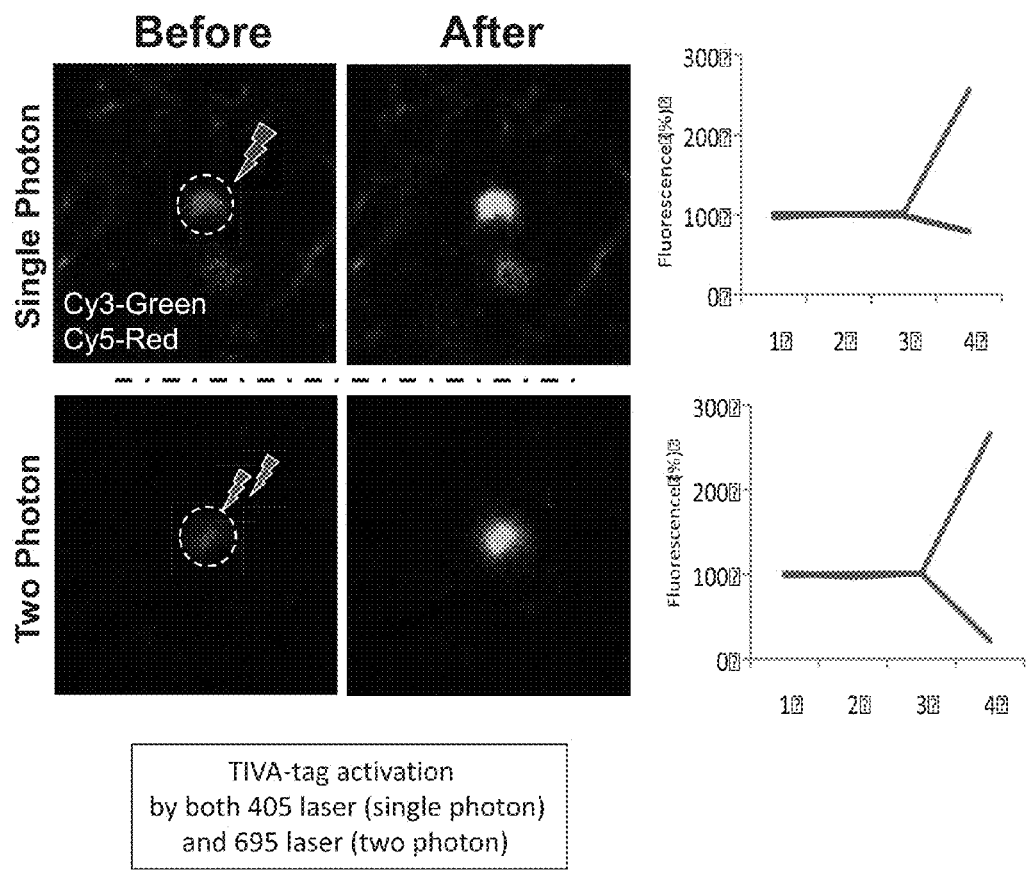
FIG. 17 is a set of images depicting the selective activation of the TIVA-tag in acute brain slice preparation. The upper panels demonstrate the uncaging of the TIVA-tag using a single photon 405 nm laser. The bottom panels demonstrate the uncaging of the TIVA-tag using a two-photon 695 nm laser. Activation of the TIVA-tag was measured by the change in the FRET signal from the target area.

TIVA-tag has the ability to enter cells and be activated in slice preparations. Slice preparations preserve a 3D structure of tissue, compared to traditional 2D cell culture models. Application of TIVA-tag to acute brain slice preparations demonstrated that TIVA-tag can be activated in cells with both single photon and two photon stimulation. For single photon activation, a 405 nm laser line was used. For two photon activation, a 695 nm laser was used. In both cases, targeted irradiation cleaved the photocleavable linker of the TIVA-tag, thereby uncaging and activating the TIVA-tag. Activation of the TIVA-tag was measured by changes in the FRET signal in the targeted area. Before activation, Cy5 dominated in the target area. Following activation, the Cy5 signal decreased, while the Cy3 signal increased (FIG. 17), indicating that the TIVA-tag was cleaved at the photocleavable linkers.

Figure 18:
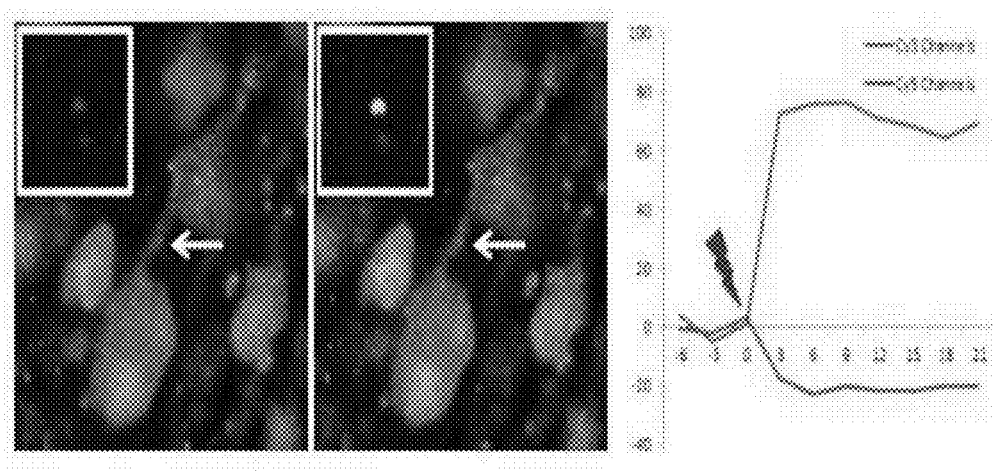
FIG. 18 depicts the results of an example experiment demonstrating the activation of the TIVA-tag in a single dendrite in live slice preparation. The inset shows a single cell soma in the slice that fluoresces after activation by photo-uncaging. The graph on the right quantitates this change in fluorescence emission in arbitrary units. This slice is from a 60 day old adult mouse.

In another experiment, TIVA-tag was activated in a single dendrite and a single soma from a live slice preparation. The slice was obtained from a 60-day old adult mouse. TIVA-tag in a single dendrite was uncaged (FIG. 18, arrow). The inset in FIG. 18 depicts a single cell soma in the slice that changes fluorescence after the TIVA-tag in the soma is activated by UV-uncaging (FIG. 18). When fluorescence is quantified, UV-uncaging resulted in an increase in the Cy3 signal with a concurrent decrease in Cy5 signal, indicating the activation of the TIVA-tag (FIG. 18).

Example 5

TIVA-Nuc

In some instances TIVA-tag is designed to have the ability to enter and/or be activated in a specific subcellular compartment, for example, the nucleus, allowing for the analysis of RNA transcripts in that specific compartment only. Activation of TIVA-tag in the nucleus (TIVA-nuc) is described here.

Given the exquisite spatial resolution of TIVA-tag it was also applied to the nuclear subcompartment of neurons so that the nuclear complement of RNA is captured at specified times after cellular stimulation. To illustrate this approach live acute brain slice from the hippocampus of C57/B16 mice were treated with the Hoechst dye (a vital nuclear stain) that permits visualization of the nucleus (FIG. 19).

The specific laser line used to activate the TIVA-tag is dependent on the target desired (whole nucleus or nucleosome). For example, in some instances TIVA-tag to be activated in the nucleus is activated by a fs-pulsed IR laser capable of two-photon excitation. The choice of the laser line is made to achieve the optimal spatial resolution of the uncaging location. The location of TIVA-tag loading was visualized and displayed as a pseudocolor image (FIG. 19). The TIVA-tag was photoactivated solely in the nucleus as depicted. The uncaging site is defined by the target area of the laser, and is defined as the white dot inside the nuclear boundaries in FIG. 19. The nuclear TIVA-signal changes from a FRET signal to an uncaged signal as depicted by the lower panels. Activation of the TIVA-tag in the nucleus is visualized by the change in the FRET signal observed in the target area of the nucleus. Before uncaging of the TIVA-tag, the target area fluorescence was dominated by Cy5. Following activation, fluorescence was changed to that dominated by Cy3. The graphs on the right side of FIG. 19 quantify the uncaging event through measurement of the reduced FRET signal as well as the increased Cy3 signal.

The change in fluorescence in the Cy3 and Cy5 channels indicates successful uncaging of the TIVA-tag. Further, the changes in fluorescence were observed primarily in the nucleus and not in the cytosol, indicating the successful activation of TIVA-tag specifically in the nucleus.

Figure 19:
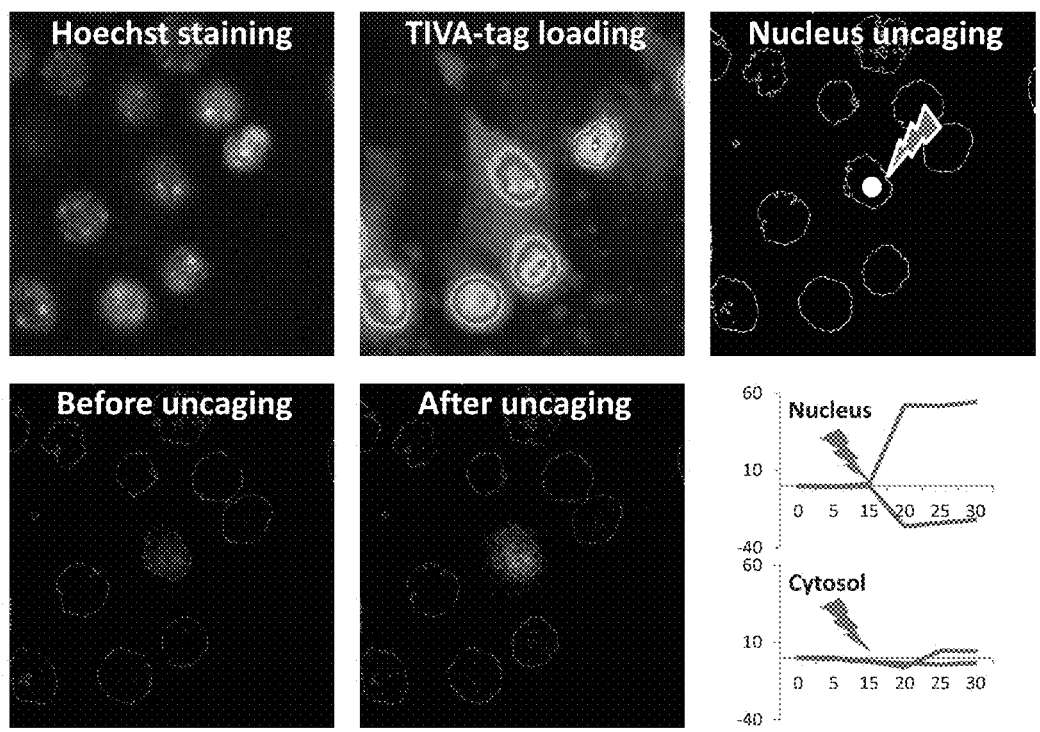
FIG. 19 depicts the results of an example experiment demonstrating the activation of TIVA-tag specifically in the nucleus of a cell (TIVA-nuc). Hoechst staining was used to define the nucleus of live cells. The uncaging target within the nuclear boundary is defined as the dot in the upper right image. Changes in the FRET signal after irradiation signifies the successful activation of the TIVA-tag in the nucleus. Quantification of the FRET signals shows that activation occurred specifically in the nucleus, and not in the cytosol.

Also shown in FIG. 19 is the appearance of Cy3 signal in the cytoplasm, ~25 mins after photoactivation of TIVA-tag in the nucleus. This represents the time for the photoactivated TIVA-tag to move from the nucleus into the cytoplasm. It is not currently known if this is TIVA-tag-nuclear RNA complex or TIVA-Cyt (cytoplasm) by itself.

Figure 20:
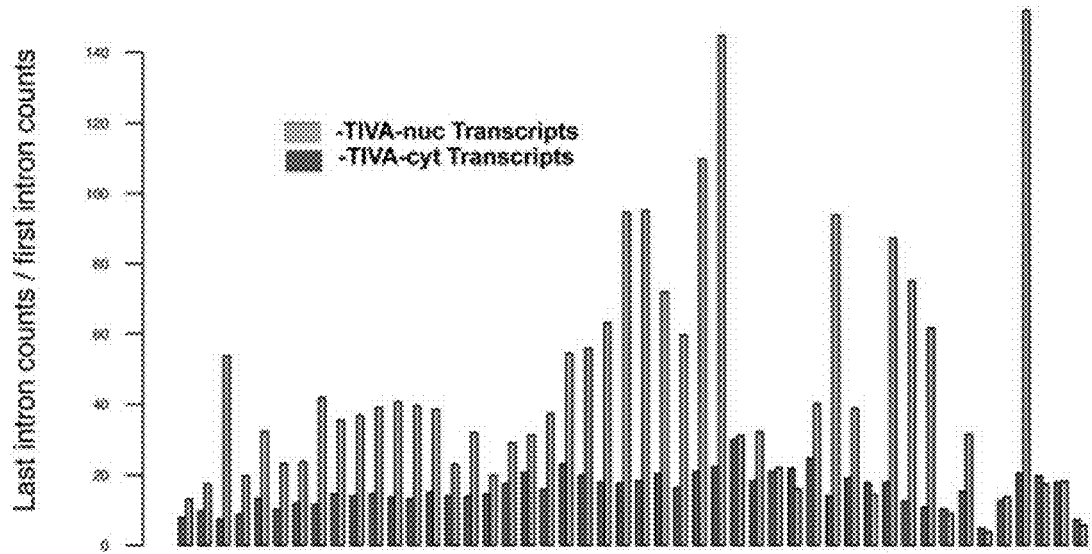
FIG. 20 depicts the results of an example experiment demonstrating TIVA-nuc transcriptome analysis. When TIVA-tag is activated in the nucleus or cytoplasm of a single cell, there is a distinction in the number of introns, showing that the TIVA-nuc procedure is isolating hnRNAs.
Figure 20:
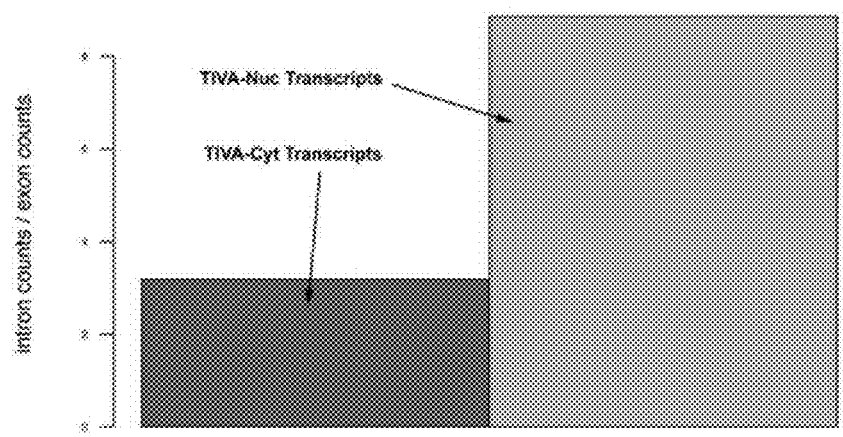

To show the feasibility of using TIVA-Nuc to isolate the RNA from a single nucleus, data in FIG. 20 shows that RNA isolated from the nucleus contains a higher proportion of introns then that isolated from the cytoplasm. As nuclear hnRNAs will by definition have a large number of intronic sequences in the primary transcript this is one way of assessing whether or not TIVA-Nuc can isolate these initial transcripts. Indeed the top panel shows the higher ratio of read counts for the last intron (3') relative to the first intron (5') for the TIVA-Nuc sample as compared to the cytoplasmic mRNA for 50 randomly selected genes. The bottom panel shows a graphical representation of intron/exon counts for the total population of transcripts.

The data presented herein indicate that TIVA-tag can enter and be activated in the nucleus, in a process referred to as TIVA-nuc. This allows the harvesting of nuclear RNA. TIVA-nuc can therefore enrich newly transcribed mRNAs in the nucleus. This process allows live cell analysis of nuclear RNA, and is therefore the live cell complement of ChIP-Seq. TIVA-nuc can be used to assess RNA transcripts in activated and/or suppressed transcriptional pathways.

Example: 6

Comparison of mRNA Isolated by TIVA and Patch Pipette

Figure 21:
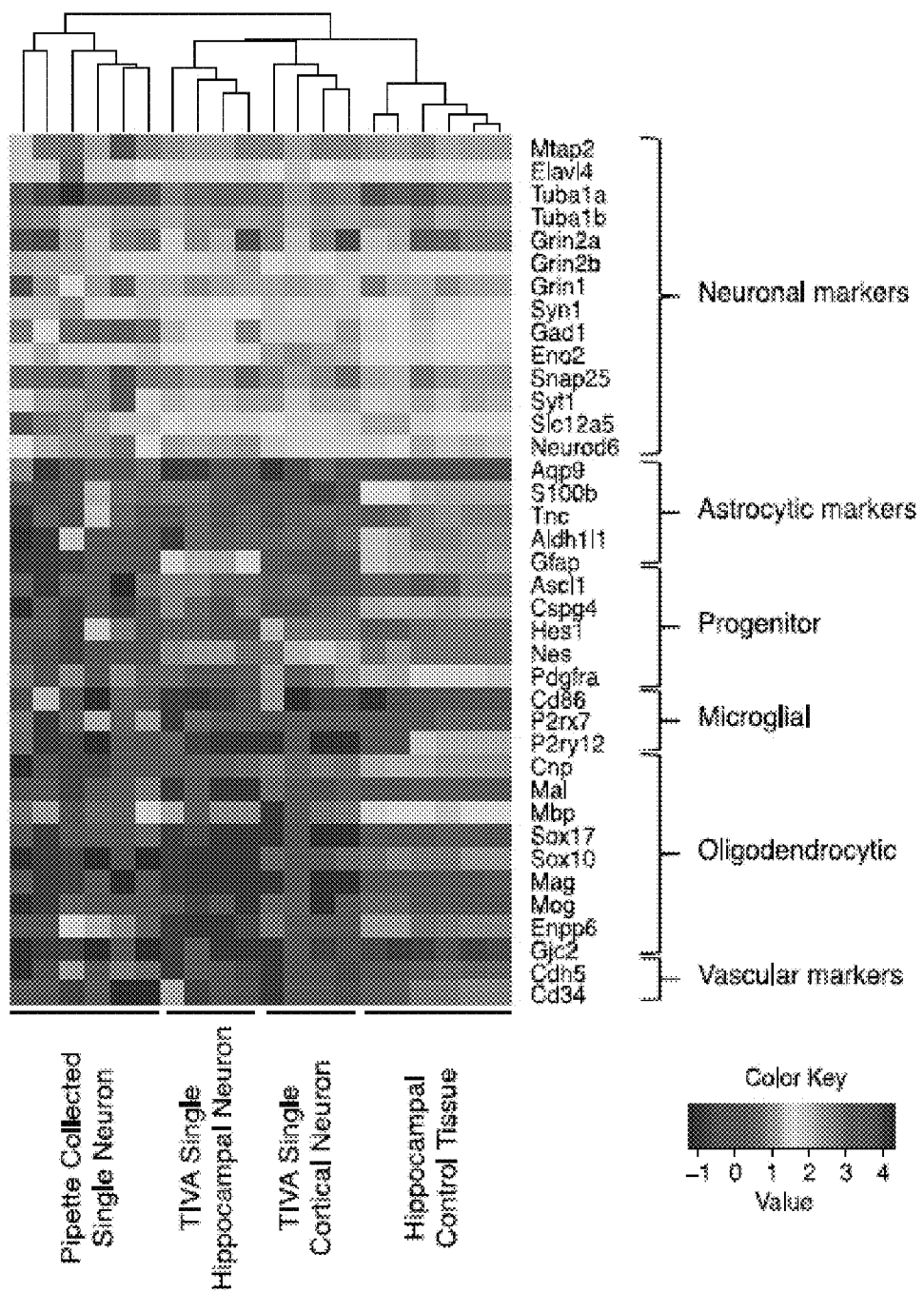
FIG. 21 depicts the results of an example experiment illustrating a heat map comparison of individual hippocampal cell mRNA harvested by TIVA or patch pipette. The genes selected for the heat map analysis represent mRNAs that are enriched in various cell types showing the reliability of TIVA and comparability to the pipette approach.
Figure 22:
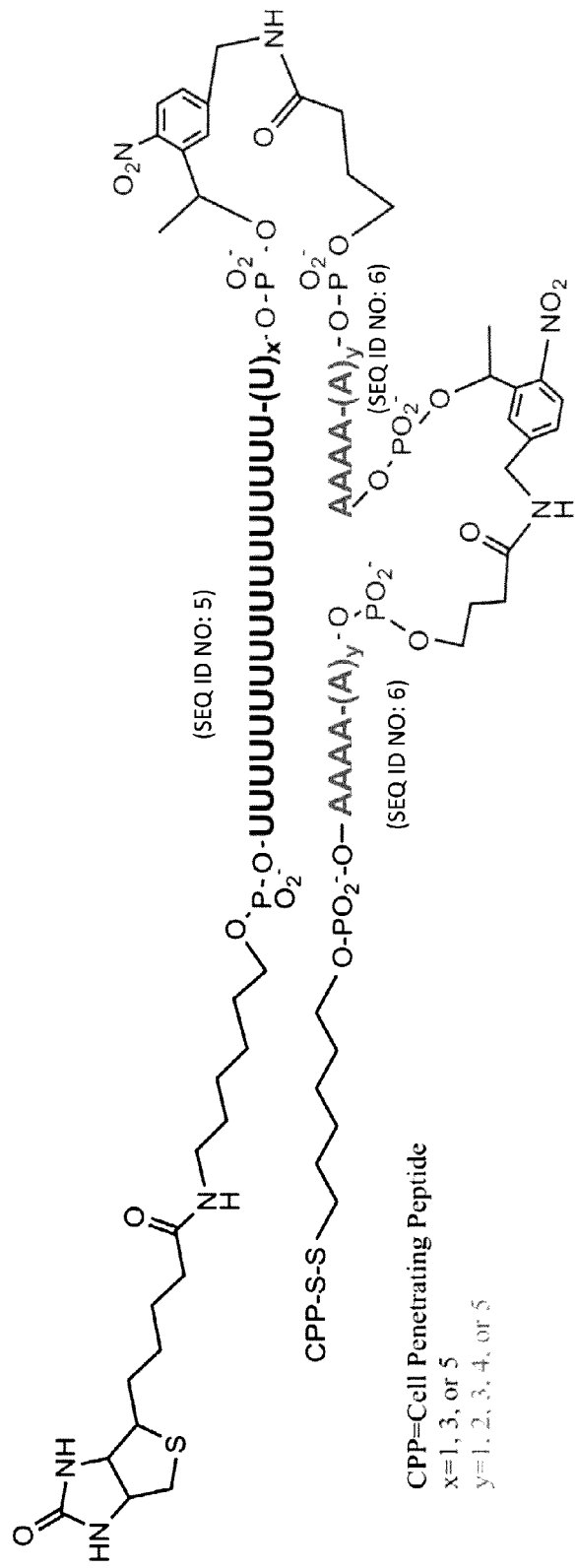
FIG. 22 is an image of the structure of an exemplary TIVA-tag structure containing a poly-U nucleic acid portion.
Figure 23:
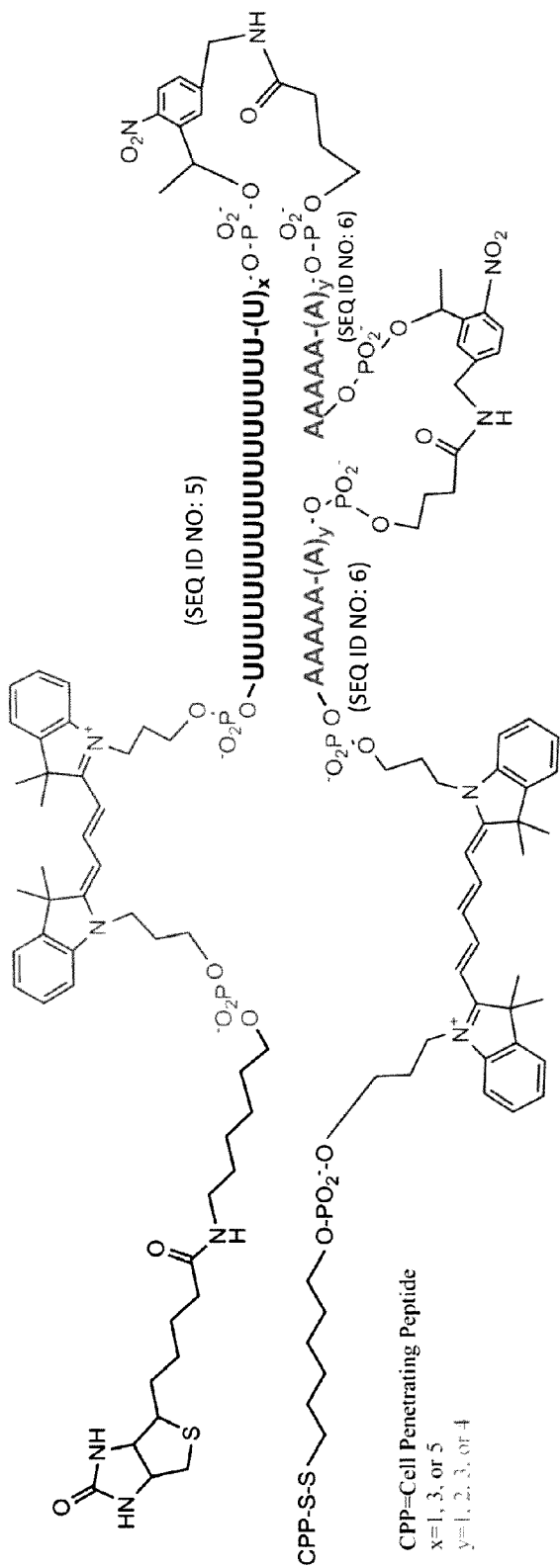
FIG. 23 is an image of the structure of an exemplary TIVA-tag structure with Cy3/Cy5 dyes, where the TIVA-tag contains a poly-U nucleic acid portion.

The mRNA captured by the TIVA-tag approach is able to be analyzed as any other single cell transcriptome sample. Antisense RNA (aRNA) amplification was used to amplify the captured mRNA and proceed to RNA-Seq analysis using either Illumina or Applied Systems NextGen sequencing platforms (Eberwine et al., 1992, Proc Natl Acad Sci USA, 89: 3010-3014; Phillips and Eberwine, 1996, Methods, 10(3): 383-288; Morris et al., 2011, Journal of Visualized Experiments, (50), e2634). The amplified RNA made from TIVA-tag captured mRNA is indistinguishable from that of standard patch pipette isolated material. Indeed when the TIVA-tag is activated in a single cell in a field of 100,000 primary cells and then the whole culture harvested and the biotin-associated TIVA-tag captured mRNA from the single cell is isolated, amplified, and NextGen sequenced its expression profile is clearly that of a neuron as evidenced by the marker gene heat map shown in FIG. 21. As the primary cell cultures are co-cultures of neurons, astrocytes and endothelial cells markers for these other cell types are also included to show the ability to mRNA from a single activated cell with little to no contamination from the other surrounding cells. The hippocampal total tissue is a control showing the profile of the mixed cell types. Also as the TIVA-tag isolated RNA gives a profile similar to that of the patch pipette isolated mRNA this shows that the TIVA approach is as specific as that of pipette isolate and much easier.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A hybrid nucleic acid molecule comprising:
    a) a first, second, and third oligomer, wherein the first oligomer is linked to the second oligomer through a first photocleavable linker and the second oligomer is linked to the third oligomer through a second photocleavable linker, wherein the first, second, and third oligomers are arranged in a caged hairpin conformation wherein the second oligomer comprises a poly-A nucleic acid sequence, comprising at least 7 consecutive adenosines, that is complementary to a first nucleic acid sequence of the first oligomer, such that the first oligomer is hybridized to the second oligomer, and wherein the third oligomer comprises a poly-A nucleic acid sequence, comprising at least 7 consecutive adenosines, that is complementary to a second nucleic acid sequence of the first oligomer, such that the first oligomer is hybridized to the third oligomer;
    b) a label for isolating nucleic acids, wherein the label is linked to the first oligomer;
    c) a cell penetrating domain (CPD).

2. The molecule of claim 1, wherein the first oligomer comprises a nucleic acid sequence comprising at least 18 consecutive 2'-fluoro nucleotides, wherein the second oligomer comprises a poly-A nucleic acid sequence comprising at least 7 consecutive adenosines, and the third oligomer comprises a poly-A nucleic acid sequence comprising at least 7 consecutive adenosines.

3. The molecule of claim 1, wherein the first oligomer comprises nucleic acid sequence comprising at least 18 consecutive 2'-fluoro nucleotides, wherein the second oligomer comprises a poly-A nucleic acid sequence, comprising at least 14 consecutive adenosines, and the third oligomer comprises a poly-A nucleic acid sequence, comprising at least 14 consecutive adenosines.

4. The molecule of claim 1, wherein the molecule is caged in the absence of cleavage of the photocleavable linker.

5. The molecule of claim 1, wherein the label is biotin.

6. The molecule of claim 1, wherein the CPD is linked to the third oligomer.

7. The molecule of claim 1, wherein the CPD is a cell-penetrating peptide.

8. The molecule of claim 1, wherein the CPD comprises folate.

9. The molecule of claim 1, wherein the CPD is a compound that specifically directs the entry of the molecule into a specific cell population.

10. The molecule of claim 1, wherein the CPD directs entry of the molecule into a subcellular compartment selected from the group consisting of nucleus, nucleosome, mitochondria, chloroplast, dendrite, soma, and lysosome.

11. A method of isolating nuclear RNA in a live cell, the method comprising the steps of: introducing the hybrid nucleic acid molecule of claim 1 into the nucleus of the cell, activating the molecule in the nucleus under conditions suitable for binding of the nucleic acid portion of the hybrid molecule to nuclear RNA, wherein the activation cleaves the photocleavable linkers in the molecule;

allowing the formation of a hybridized nucleic acid molecule/nuclear RNA complex; and isolating the hybridized nucleic acid molecule/nuclear RNA complex.

12. The method of claim 11, wherein the first oligomer is at least an 18mer 2'-fluoro, wherein the second oligomer is at least a poly-A 7mer, and the third oligomer is at least a poly-A 7mer.

13. The method of claim 11, wherein the first oligomer is at least an 18mer 2'-fluoro, wherein the second oligomer is at least a poly-A 14mer, and the third oligomer is at least a poly-A 14mer.

14. The method of claim 11, wherein the molecule is caged in the absence of cleavage of the photocleavable linker.

15. The method of claim 11, wherein the molecule is uncaged in the presence of cleavage of the photocleavable linker.

16. The method of claim 11, wherein the label is linked to the first oligomer.

17. The method of claim 11, wherein the label is biotin.

18. The method of claim 11, wherein the CPD is linked to the third oligomer.

19. The method of claim 11, wherein the CPD is a cell-penetrating peptide.

20. The method of claim 11, wherein the CPD comprises folate.

21. The method of claim 11, wherein the CPD directs the entry of the molecule into a specific cell population.

22. The method of claim 11, wherein the CPD directs entry of the molecule into the nucleus of a cell.

23. The method of claim 11, wherein activating the molecule comprises cleavage of the photocleavable linker.

24. The method of claim 23, wherein cleavage of the photocleavable linker comprises administering ultraviolet light to the nucleus.

25. The method of claim 23, wherein cleavage of the photocleavable linker comprises administering light to the nucleus, wherein the light has a wavelength of about 350 nm-1500 nm.

26. The method of claim 23, wherein cleavage of the photocleavable linker comprises exposing the nucleus to two photon excitation of near-infrared or infrared light.

* * * * *

UNITED STATES PATENT AND TRADEMARK OFFICE
CERTIFICATE OF CORRECTION

PATENT NO. : 9,540,680 B2
APPLICATION NO. : 13/838504
DATED : January 10, 2017
INVENTOR(S) : James Eberwine et al.

Page 1 of 1

It is certified that error appears in the above-identified patent and that said Letters Patent is hereby corrected as shown below:

In the Specification

Column 1, Lines 18-24 should read as follows:
STATEMENT REGARDING FEDERALLY SPONSORED RESEARCH OR DEVELOPMENT
This invention was made with government support under grant numbers AG009900, DO041117, and GM083030 awarded by the National Institutes of Health. The government has certain rights in the invention.

Signed and Sealed this
Twelfth Day of February, 2019

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: chemically synthesized

<400> SEQUENCE: 1
tttttttttt tttttttt                                                   18

<210> SEQ ID NO 2
<211> LENGTH: 7
<212> TYPE: DNA
<213> ORGANISM: Artificial Sequence
<220> FEATURE:
<223> OTHER INFORMATION: Chemically Synthesized

<400> SEQUENCE: 2 aaaaaaa                                                                7

<210> SEQ ID NO 3
<211> LENGTH: 217
<212> TYPE: DNA
<213> ORGANISM: Artificial Sequence
<220> FEATURE:
<223> OTHER INFORMATION: chemically synthesized

<400> SEQUENCE: 3
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaa                             217
```

```
<210> SEQ ID NO 4
<211> LENGTH: 18
<212> TYPE: RNA
<213> ORGANISM: Artificial Sequence
<220> FEATURE:
<223> OTHER INFORMATION: chemically synthesized

<400> SEQUENCE: 4
uuuuuuuuuu uuuuuuuu                                              18

<210> SEQ ID NO 5
<211> LENGTH: 22
<212> TYPE: RNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (18)..(22)
<223> OTHER INFORMATION: these nucleotides may be absent

<400> SEQUENCE: 5
uuuuuuuuuu uuuuuuuuuu uu                                         22

<210> SEQ ID NO 6
<211> LENGTH: 9
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (6)..(9)
<223> OTHER INFORMATION: These nucleotides may be absent

<400> SEQUENCE: 6 aaaaaaaaa                                                         9
```